US010281745B2

(12) United States Patent
Knoll

(10) Patent No.: US 10,281,745 B2
(45) Date of Patent: May 7, 2019

(54) ELECTRONIC SPECTACLES

(71) Applicant: INOPTEC LIMITED ZWEIGNIEDERLASSUNG DEUTSCHLAND, Zolling (DE)

(72) Inventor: Ralf G. J. Knoll, Zolling (DE)

(73) Assignee: Inoptec Limited Zweigniederlassung Deustchland, Zolling (DE)

( * ) Notice: Subject to any disclaimer, the term of this patent is extended or adjusted under 35 U.S.C. 154(b) by 121 days.

(21) Appl. No.: 15/313,469

(22) PCT Filed: May 28, 2015

(86) PCT No.: PCT/EP2015/061918
§ 371 (c)(1),
(2) Date: Nov. 22, 2016

(87) PCT Pub. No.: WO2015/181340
PCT Pub. Date: Dec. 3, 2015

(65) Prior Publication Data
US 2017/0199396 A1    Jul. 13, 2017

(30) Foreign Application Priority Data
May 28, 2014  (DE) .......................... 10 2014 107 587
Jun. 11, 2014  (DE) .......................... 10 2014 108 190

(51) Int. Cl.
G02B 27/14  (2006.01)
G02C 7/10  (2006.01)
(Continued)

(52) U.S. Cl.
CPC .............. *G02C 7/101* (2013.01); *A61B 3/113* (2013.01); *A61F 9/023* (2013.01); *A63B 33/002* (2013.01);
(Continued)

(58) Field of Classification Search
CPC ...................................................... G02C 7/101
USPC ........................................................ 359/630
See application file for complete search history.

(56) References Cited

U.S. PATENT DOCUMENTS 2,066,680 A    10/1934   Gieskieng
5,172,256 A    12/1992   Sethofer
(Continued)

FOREIGN PATENT DOCUMENTS

DE        2 001086 A     7/1971
DE        2001086 A1     7/1971
(Continued)

OTHER PUBLICATIONS

Adrian, W. and Bhanji, A.: "Fundamentals of disability glare. A formula to describe stray light in the eye as a function of the glare angle and age." Proceedings of the First International Symposium on Glare, 1991, Orlando, Florida, pp. 185-194.
(Continued)

*Primary Examiner* — James Jones
(74) *Attorney, Agent, or Firm* — Steven M. Shape; Dennemeyer & Associates, LLC

(57) ABSTRACT

The invention relates to spectacles. Said spectacles comprise a spectacle lens having a liquid crystal cell (LC) the transmission (TR) of which can be switched between transmitting and blocking. Furthermore, the spectacles comprise an eye tracker (ET) which can detect the viewing direction of the eye. They further comprise at least one sensor (IL, IR) for measuring the brightness of the visible light incident on it, said sensor being arranged on the eye side of the spectacle lens and measuring the brightness entering through the at least one spectacle lens in a spatially resolved manner. The sensor can determine the brightness of the visible light incident on it from the viewing direction of the eye detected by the eye tracker. The spectacles also have a closed loop
(Continued)

control system for controlling the transmission of the liquid crystal cell, a desired value for the brightness at the level of the eye being predetermined, and the closed loop system using the brightness measured by the sensor in the viewing direction of the eye as the actual value.

22 Claims, 12 Drawing Sheets

(51) Int. Cl.
    *A61F 9/02* (2006.01)
    *A61B 3/113* (2006.01)
    *A63B 33/00* (2006.01)
    *G02B 27/01* (2006.01)
    *G02C 11/04* (2006.01)
    *G02C 11/00* (2006.01)
    *G02F 1/133* (2006.01)

(52) U.S. Cl.
    CPC .......... *G02B 27/0172* (2013.01); *G02C 11/04* (2013.01); *G02C 11/10* (2013.01); *G02F 1/13318* (2013.01); *A63B 2033/004* (2013.01); *G02B 2027/0178* (2013.01); *G02C 2202/18* (2013.01); *G02F 2001/13312* (2013.01)

(56) References Cited

U.S. PATENT DOCUMENTS

| | | |
|---|---|---|
| 5,305,012 A | 4/1994 | Faris |
| 5,654,786 A | 8/1997 | Bylander |
| 7,970,172 B1 | 6/2011 | Hendrickson |
| 2004/0012762 A1 | 1/2004 | Faris |
| 2009/0302197 A1* | 12/2009 | Uchino ................ H04N 5/2254 250/201.4 |
| 2013/0194244 A1* | 8/2013 | Tamir .................... G02B 23/12 345/207 |
| 2013/0293379 A1 | 11/2013 | Rains, Jr. et al. |

FOREIGN PATENT DOCUMENTS

| | | |
|---|---|---|
| DE | 199077334 A1 | 8/2000 |
| DE | 10134770 A1 | 7/2001 |
| DE | 102012217326 A1 | 3/2014 |
| EP | 0813079 A2 | 12/1997 |
| EP | 1275556 A2 | 1/2003 |
| FR | 2988333 A | 9/2013 |
| GB | 2420183 A | 5/2006 |
| GB | 2445365 A | 7/2008 |
| JP | H0882751A A | 3/1996 |
| WO | 2013/143998 A2 | 10/2013 |

OTHER PUBLICATIONS

Douglas Mace, Philip Garvey, Richard J. Porter, Richard Schwab, Werner Adrian: „Counter-measures for Reducing the Effects of Headlight Glare; Prepared for: The AAA Foundation for Traffic Safety, Washington, D.C., Dec. 2001.

Prof. Dr.-Ing. Gert Hauske: "Systemtheorie der visuellen Wahrnehmung", Teubner Verlag, Stuttgart, 1994.

* cited by examiner

ELECTRONIC SPECTACLES

FIELD OF THE INVENTION

The invention relates to electronic spectacles and a system for glare suppression.

STATE OF THE ART

The light intensity passing through a light modulator may be electrically controlled with the aid of diverse liquid crystal cells (TN, STN, Fe-LC, etc.) that are available on the market in such a way that at least two states are reached, namely permeable transparent or impermeable dark—as is the case with current active 3D television or cinema spectacles (so-called shutter goggles).

According to this basic idea, attempts were already made in the 1960s to develop "electronic sunglasses" in order to offer the wearer of such glasses a variable transmission.

Some known electronic sunglasses operate with a pure control (instead of regulation), i.e. the photosensors lie on the outside of the spectacles, so that only the brightness that is incident on the spectacles from the outside is measured (see, for example, U.S. Pat. No. 5,172,256 or DE 10 2012 217 326 A1). Accordingly, a characteristic line which is only based on pure experience values correspondingly switches an LCD to light or dark.

In addition, there are often too few sensors whose reception direction is also non-specific (the sensors point forward or towards the sky). This often leads to completely wrong, and even contrary, reactions of the glasses. For example, if the wearer looks into a dark area of observation (dark corner), while at the same time the spectacles are caught by a stray beam of sunlight (through chance reflections on objects or moving leaves in the forest which have a fine dark pattern), the LC is dark, although it should actually be bright because the wearer wants to see the dark area.

Electronic systems for suppressing glare with the aim of visual enhancement have been around for more than 80 years (see, for example, U.S. Pat. No. 2,066,680 A). In this patent of 1934, the light disc performs exactly the same in front of the field of view of the user (visor), i.e. with precisely the same frequency and phase position, wherein the outside world is perceived by the user synchronously with the modulated headlamp light.

If the user's visor, for example, is closed for 50% of the time (pulse-pause ratio=1:1), 50% of the unwanted light (e.g. low-level sunlight) is suppressed, and the visibility of the object to be viewed is augmented.

Later, electronically-controllable light modulators replaced mechanical light modulators, in particular in the form of liquid crystal cells, while the light sources became also increasingly faster and more easily controllable electronically (see, for example, DE 101 34 770 A1, DE 2 001 086 A, WO 2013/143 998 A2).

OBJECT

The object of the invention is to provide spectacles and systems which provide visual improvements for the spectacle wearer under different conditions.

SOLUTION

This object is achieved by the subject matter of the independent claims. Advantageous further developments of the subject matter of the independent claims are characterized in the subclaims. The wording of all claims is hereby incorporated by reference into the content of this description.

In the following sections, different aspects are described which solve the problem or contribute to its solution. It will be clear to a person skilled in the art that almost all of these different aspects may be combined with one another.

Eye-Tracker

To achieve the object, spectacles with at least one eye are proposed for a wearer. The spectacles have at least one spectacle lens, wherein the at least one spectacle lens has a liquid crystal cell, the transmission of which may be varied by a suitable control. Furthermore, the spectacles have an eye tracker, which may determine the viewing direction of the eye. Furthermore, there is at least one sensor for measuring the brightness of the visible light incident thereon, wherein the sensor is arranged on the eye-side of the spectacle lens, through which the brightness through the at least one spectacle lens may be measured, and an imaging system with a camera, or
at least three sensors that span a coordinate system, or
a compound eye.

An electronic compound eye consists of many individual eyes, similar to the term "ommatidia" used in biology for the description of a compound eye of flying insects, but consisting of electrical photosensors, which are again positioned at the lower end of light-conducting funnels (without lenses), or, respectively, with an upstream micro-lens or a combination of both (funnel and micro-lens) (see, for example, EP 0813079 A2).

The at least one sensor can determine the brightness of the visible light from the viewing direction of the eye which is determined by the eye tracker.

The spectacles also have a closed-loop control circuit for regulating the transmission of the liquid crystal cell, wherein a setpoint value is set for the brightness at the eye, and wherein the control loop uses the rightness measured by the sensor in the viewing direction of the eye as the actual value.

With such spectacles, the brightness may be adjusted quickly and precisely to the glare coming from the actual viewing direction of the spectacle wearer, for example when a car driver is approaching another car or when a driver drives into a tunnel or drives out of a tunnel on a sunny day.

However, today, in the context of extreme miniaturization and "wearable electronics", it is possible to implement such powerful and safe systems for visual improvement by means of miniature electronics, which may also be easily and simply integrated into spectacles.

In order to extend the scope of the spectacles, it is advisable not to adjust the transmissivity of the liquid crystal cell of the spectacles to a suitable gray scale, but to switch the spectacles between a light transmitting period and a light blocking period in as short a sequence as possible. In order that the human eye perceives as little as possible of this switching, a cycle (period) of a transmitting period and a blocking period should last a maximum of one twenty-fourth ($\frac{1}{24}$) of a second.

Such systems work particularly well when a person no longer perceives the regulation, i.e. working with cycle times above the critical flicker frequency (CFF) of approximately 60 Hz.

To achieve this, the liquid crystal cell should be so designed that it can change its transmission from 90% to 10% and from 10% to 90% in a maximum of 10 ms.

If such a liquid crystal cell is used, the transmission of the liquid crystal cell may be switched between high and low transmission states. For this purpose, there must be means for controlling or regulating the times of the states of high and low transmission of the liquid crystal cell, as well as the change between these two states. The regulation or closed-loop control circuit is appropriately designed in such a way that the times of the state of high transmission become shorter (pulse width modulation, PWM) with increasing brightness of the visible light incident on the at least one sensor.

The control is even more precise and even more gentle for the eyes of the spectacle wearer if the control circuit is so designed that it can take into account a user-specific eye/retina sensitivity curve for weighting the brightness when determining the brightness from the viewing direction of the eye.

The user-specific eye/retina sensitivity curve takes into account e.g. the age of the spectacle wearer, other general and/or individual eye-specific parameters, in particular with respect to the angle of incidence, but also with respect to other light-technical variables which have an influence on the perception, e.g. brightness, distance of the light source or light intensity or light strength (light flux per angle of steradia), illumination level, their respective absolute magnitudes such as threshold at the eye, light flux, size of the interference source (point vs. surface), color or spectral distribution of the source and its temporal variation, presetting of the eye (photoptic vs. scotopic vision, etc.).

These sensitivity curves may be determined heuristically and logically, but are usually determined empirically, as for example used and analyzed in: Douglas Mace, Philip Garvey, Richard J. Porter, Richard Schwab and Werner Adrian: "Counter-measures for Reducing the Effects of Headlight Glare"; Prepared for: The AAA Foundation for Traffic Safety, Washington, D.C., December 2001.

The aforementioned sensitivity curves of the human eye are stored as weighting factors in various tables (lookup table—LUT) or as a calculable formula—at least in such a way that in the closed-loop control circuit of the system, comprising an internal sensor, a microcontroller and the preset setpoint value, these weighting factors are incorporated in real time into the setting signal to set the transmission of the liquid crystal cell.

For example, a formula by Adrian and Bhanji (Adrian, W. and Bhanji, A. (1991) "Fundamentals of disability glare. A formula to describe stray light in the eye as a function of the glare angle and age." Proceedings of the First International Symposium on Glare, Orlando, Fla., pp. 185-194) for the determination of the "impossible visibility and recognisability of 5 objects in the case of disability glare", takes into account the dependence on the angle of incidence of the light in the eye under which there is progressively no longer recognition.

EXAMPLE

If incident light falls directly perpendicularly to the eye, the glare is highest (maximum in the weight formula). After the eye tracker has determined the direction of view (vector ET(x,y,z)), and the internal sensor and/or the external sensor has determined the direction of the incident light (vector glare (x,y,z)), the microcontroller can check whether these two vectors are collinear, i.e. have the same direction, and accordingly evaluate the maximum with the aforementioned weight equally. If, for example, the weight curve is stored as an LUT, then the latter moves correspondingly virtually back and forth in the memory of the microcontroller with the viewing direction vector ET(x,y,z) of the eye movement. If it is stored as a formula, the vector is correspondingly converted into an angle.

As a result, the sensitivity curves need no longer be made as special pre-lenses (for example, individual free-form plastic lenses) which correspondingly "weight" the light before it hits a photosensor. Weight-bearing lenses, or even moving lenses, which reproduce the sensitivity of the retina, may be dispensed with, since everything is represented purely in software, while all sensors are rigidly mounted.

The fact that the spectacles have a spectacle frame that seals the eye associated with the at least one spectacle lens in a light-tight manner against the ambient light, is particularly gentle for the eye and results in particularly precise regulation.

The setting of the setpoint value of the control circuit at an average brightness in the range of 20 to 400 lx (Lux) has proved to be particularly gentle for the eye. Such a value allows control to a constant brightness for the eye of the spectacle wearer when the external brightness changes from very bright down to the setpoint value or vice versa, for example when a car enters or leaves a tunnel on a summer day. The changes in the brightness, or the illumination intensity, may be a factor of 1000 or more at such a moment. The spectacle wearer is not exposed to these very fast brightness fluctuations. The latter are always balanced by the control of the spectacles.

The entrance into a dark tunnel or dark shadow area (forest etc.) on a bright sunny day is a typical application. Since the setpoint value set here during the day corresponds to dark sunglasses, the eye is always adapted to the dark and prepared from the outset, so that upon entering the dark area, the spectacle lens only needs to be regulated in real-time to be more transparent and clear (open) in order to be able to see immediately in the dark. The dark adaption time of the human eye required without these spectacles is about seconds, wherein this is thus reduced to a fraction of a second (for example, 10 ms) so that one may immediately see in the dark. Exactly the reverse occurs upon exiting the tunnel back into the light.

Further control possibilities, which are described below, become available if the spectacle lens has at least one further brightness sensor which is arranged on the side of the spectacle remote from the eye (external sensor) to determine the brightness of the ambient light.

For example, the setpoint value of the control circuit may then be changed as a function of the brightness of the ambient light, wherein such a change of the setpoint value is slower by a factor of at least ten than the control of the transmission of the liquid crystal cell, and thus should take place so that the eye of the spectacle wearer may adapt without difficulty to this change.

In the event of sudden changes in brightness, the spectacles should react within 10 ps to one second in such a way that the liquid crystal cell (LC) is set to the low transmittance state.

In extreme situations, such as the so called "disability glare", wherein the spectacle wearer is not able to read or see anything (see above), i.e. when an extremely strong glare occurs exactly perpendicular to the eye (below zero degrees), such as looking directly into the sun, the spectacles are completely closed, i.e. set to completely black.

Such control is not critical in that it does not matter whether one sees nothing because of the extreme glare or because the spectacles darken to blackness; however, the latter state has the advantage that the eye remains protected and remains adapted to the dark.

After a certain period of time or a change in the direction of the eye of the spectacle wearer, the spectacles are then slowly returned to light.

The control of the glare suppression is even more precise, when the spectacles have two spectacle lenses for two eyes of a spectacle wearer, as well as one eye sensor on each spectacle lens for measuring the brightness of the visible light striking the respective eye. The control may then be performed individually for each eye by means of a control circuit for each spectacle lens.

A gain in the brightness/contrast range may be achieved with such spectacles if the setpoint values for the two eyes deviate from one another by 1% to 60%. In practice, typical values for the right-left deviations are 5%-30%. In analogy to high-dynamic range (HDR) photography, "HDR vision" may be referred to here.

Previously, such systems have been available theoretically, but only now, through the availability of extremely fast modulators and very fast processors, may intelligent and safety-relevant multi-channel real-time control systems be implemented for visual enhancement, wherein the left and right eyes are separated and/or multiple users may be included for group applications.

To ensure this, the control of the brightness of the visible light incident on the one eye should be taken into account when controlling the brightness for the other eye.

The spectacles may also be combined with a light source which is arranged on the side of the spectacles facing away from the eye. The light source is then appropriately controlled depending on the viewing direction of the spectacle wearer. In this way, darkening caused by the shuttering of the spectacles in order to avoid glare may be counteracted. For example, four LEDs are conceivable, one at each eye corner.

The eye tracker then determines which one of the four LEDs should be energized depending on the viewing direction—either only one LED in the direction of view, looking outwards upwards/downwards—or two LEDs corresponding to the viewing direction—or all four LEDs while looking straight ahead.

Further Possibilities:

Instead of, or in addition to, four rigidly-mounted LEDs at the corners of a pair of spectacles, any other light sources/headlights may also be controlled in the direction of the eye with the help of the eye tracker.

For this purpose, these lamps may be pivoted electromechanically, in a similar manner to the electronically pivoting curve light for motor vehicles, or in the case of pivoting 3-axis monitoring cameras, or in the case of freely movable hand-held systems, which may be controlled by means of electronic or mass-bearing gimbals (gimbal or steady-cam method), which maintain their own stable coordinate system with respect to the earth or wearer, and with respect to which, the headlamp may then pivot in the viewing direction.

Thus, all types of LED headlights in all kinds of supports may be considered: car, helmet, bike, motorcycle, hand, shoulder, body, rifle, etc.

This is particularly effective when the luminance times and the luminous intensity of the light source are so controlled that the light source illuminates during the times of the state of high transmittance of the liquid crystal cell. In this case, the temporal integral of the product of the luminous intensity of the light source and the transmission of the liquid crystal cell should remain constant within a predetermined tolerance during a change in the times of the state of high transmission.

Such a flashing light source may, for example, be a car headlamp which always illuminates the road and the environment with a constant brightness for the driver, while the glare caused by opposing vehicles is effectively prevented by the shuttering of the spectacles. However, other types of headlights, such as bicycle lamps, helmet lamps, flashlights, may also be used in the sense described herein.

Since the brightness detected from an external or opposing vehicle headlights is always constant under these conditions, regardless of how the pulse-pause ratio is regulated, such a car headlight may be easily replaced in the sense of a replacement strategy, or the purchase of additional headlights in the sense of a special accessories strategy.

It is only now possible to implement such powerful and safe systems for visual improvement by means of powerful white light and/or RGB LED/LASER.

In addition to car headlights, the following are also conceivable as light sources:
  a light source for illumination of a human being, an optical sensor or a camera, and/or
  a display on the side of the spectacle lens facing away from the eye. and/or
  a display on the eye-side of the spectacle lens, and/or
  a head-up display.

For example, a smartphone, tablet, laptop, cockpit display, etc. may be considered as displays on the side of the spectacle lens facing away from the eye.

For example, "Google Glass" or "virtual reality" ('augmented reality') displays may be used on the eye-side of the spectacle lens.

Various displays are subsumed under head-up displays (HUD), some of them on the eye-side of the spectacles, some outside the spectacles, for example in the form of a helmet with a display. What they all have in common is that one may look through them, but the head-up display shows additional information.

All these displays may be read in the manner described above against the sun or other disturbing sources of glare.

The system may be perfectly combined with the systems and methods used for the detection of own light as described below.

In the following, individual process steps are described in more detail. The steps need not necessarily be carried out in the order indicated, while the method described may also include further steps not mentioned.

The object is also achieved by a method for controlling the brightness of the visible light incident on at least one eye, comprising the following steps:
  1. Spectacles are provided, wherein they comprise:
  1.1 at least one spectacle lens;
  1.2 wherein the at least one spectacle lens has a liquid crystal cell (LC) whose transmission (TR) may be varied by a suitable control;
  2. an eye tracker (ET) to determine the viewing direction of the eye;
  3. at least one sensor (IL, IR) to measure the brightness of the visible light incident on the sensor is provided;
  3.1 wherein the at least one sensor (IL, IR) is arranged on the eye-side of the spectacle lens;
  3.2 wherein the at least one sensor (IL, IR) measures the brightness through the at least one spectacle lens;
  3.3. wherein the at least one sensor (IL, IR) comprises
  3.3.1 an imaging system with a camera or
  3.3.2 at least three sensors which span a coordinate system or
  3.3.3 a compound eye;

3.4 wherein the at least one sensor (IL, IR) determines the brightness of the visible light which strikes it from the viewing direction of the eye determined by the eye tracker (ET);

4. a closed-loop control circuit (MC) for controlling the transmission of the liquid crystal cell (LC) is provided;

4.1 wherein a setpoint value for the brightness at the eye is preset;

4.2 wherein the control circuit takes the brightness measured by the sensor in the viewing direction of the eye as the actual value.

Improvement of the Readability of a Display Device

In order to achieve the object, a system for the improvement of visibility through glare suppression is also proposed. The system comprises:

spectacles for a wearer with at least one eye, with
at least one spectacle lens, wherein the at least one spectacle lens has a liquid crystal
cell, the transmission of which may be varied by a suitable control. The liquid crystal cell
is so designed that the transmission of the liquid crystal cell may be switched between
high and low transmission states. In this respect, the spectacles also have corresponding
means for controlling or regulating the times of the state of high transmission of the liquid crystal cell.

In addition, the spectacles have at least one sensor for measuring the brightness of the visible light incident thereon, wherein the at least one sensor is arranged on the eye-side of the spectacle lens and measures the brightness forwards through the spectacle lens.

A closed-loop control circuit regulates the transmission of the liquid crystal cell. The control is so designed that the times of the state of high transmission become shorter with increasing glare (pulse width modulation, PWM). A setpoint value is set for the brightness at the eye of the spectacle wearer, wherein the control circuit takes the brightness measured by the sensor as the actual value.

Further, the system comprises a display and means for controlling the lighting times and the luminous intensity of the display in order to illuminate during the times of the state of high transmission of the liquid crystal cell. In this case, the temporal integral of the product of the luminous intensity of the display and the transmission of the liquid crystal cell remains constant during a change in the times of the state of high transmission within a predetermined tolerance.

If, for example, the brightness of the ambient light is doubled, the system reacts, on the one hand, with a halving of the times of the state of high transmission of the liquid crystal cell, wherein the increased glare is effectively compensated. At the same time, the illumination time of the display is shortened and its luminous intensity is doubled. As a result, the brightness of the display perceived by the spectacle wearer remains unchanged.

All these processes of switching the transmission of the liquid crystal cell and switching the display on and off, should take place with such a frequency and speed that no glare or other perceptible effects occur for the wearer of the spectacles. This means that all the effects potentially perceptible to the wearer should be at least 24 Hz, preferably at least 60 Hz.

In particular, the following are considered as displays:
a display on the side of the spectacle lens facing away from the eye, and/or
a display on the eye-side of the spectacle lens, and/or
a head-up display.

A smartphone, tablet, laptop, cockpit display, etc., or a head-up display (HUD) may be
considered as displays on the side of the spectacle lens facing away from the eye.

For example, "Google Glass" or "virtual reality" ("augmented reality") may be used as a display on the eye-side of the spectacle lens.

All of these displays may be read out in the manner described, even in the event of strong solar radiation or even in the event of direct glare from the sun as a backlight.

Preferably, the spectacles comprise an eye tracker, which may determine the viewing direction of the eye. In such a case, the at least one sensor comprises:
an imaging system with a camera, or
at least three sensors that span a coordinate system;
a compound eye.

An electronic compound eye consists of many individual eyes, similar to the term "ommatidia" used in biology in the description of the compound eye of flying insects, but consisting of electrical photosensors, which are again located at the lower end of light-conducting funnels (without lens), or with respectively a preceding micro-lens, or a combination of both (funnel and micro-lens) (see, e.g. EP 0813079 A2).

The at least one sensor can determine the brightness of the visible light from the viewing direction of the eye, which may be determined by the eye tracker. The control circuit may then use the brightness measured by the sensor in the viewing direction of the eye as the actual value.

In the case of such spectacles, the brightness may be adjusted quickly and precisely to the glare coming from the actual direction of viewing of the spectacle wearer, for example if a car driver is approaching another car and irrespective of whether the driver looks in the direction of the opposing vehicle or not. Since the representation of the display is always adapted to the glare suppression performed by the spectacles, the readability of the display is never impaired.

The object is also achieved by a method which corresponds to an operation according to the principles of the described system.

Coding

The object is further achieved by a system for the improvement of visibility by means of glare suppression. The system comprises:

spectacles for a wearer with at least one eye, with
at least one spectacle lens;
wherein the at least one spectacle lens comprises a liquid crystal cell whose transmission may be varied by a suitable control;
wherein the liquid crystal cell is so designed that the transmission of the liquid crystal cell may be switched between high and low transmission states.

Further, the spectacles comprise means for controlling the times of the state of high transmission of the liquid crystal cell.

In addition, the system comprises a light source having means for controlling or regulating the luminance times and the luminous intensity of the light source so that it illuminates during the times of the state of high transmission of the liquid crystal cell. The temporal integral of the product of the luminous intensity of the light source and the transmission of the liquid crystal cell remains constant during a change in the times of the state of high transmission within a predefined tolerance.

The regulation or control of the liquid crystal cell and the light source is so designed that the temporal position of the times of the state of high transmission may be changed continuously or discontinuously within a period of times of the state of high transmission and the state of low transmission. And/or the duration of a period of the times of the state of high transmittance and the state of low transmission may be changed continuously or discontinuously.

These changes are determined by a secret coding key.

All these processes for the switching of the transmission of the liquid crystal cell and the switching on and off of the light source should take place with such a frequency and speed that no glare or any other perceptible effects occur for the wearer of the spectacles. All the effects potentially perceptible to the wearer should be at least 24 Hz, preferably at least 60 Hz.

Such coding opens up a wide range of possibilities, especially in the military and security sector (police, fire brigade, etc.). It makes it difficult for anyone not having the coding key, e.g. to eliminate glare through the light source.

In addition, the coding offers the possibility that various groups, whether they are opponents or other teams with a similar task, each receive an individually secret exclusive view via coded sources of light, in particular if outside users with very similar overall systems (visor and light source) are active at night in the same spatial region.

For the automatic control of the glare suppression, the spectacles preferably have at least one sensor for measuring the brightness of the visible light incident on the sensor. The sensor is arranged on the eye-side of the spectacle lens and measures the brightness through the at least one spectacle lens. Furthermore, the spectacles comprise a closed-loop control circuit for the control of the transmission of the liquid crystal cell in such a way that the times of the state of high transmission become shorter with increasing brightness (pulse width modulation, PWM). A setpoint value is preset for the brightness at the eye of the spectacle wearer, wherein the control loop takes the brightness measured by the sensor as the actual value.

The accuracy of the glare suppression may be increased, on the one hand, if the at least one sensor has an imaging system with a camera or at least three sensors which span a coordinate system or a compound eye. On the other hand, the spectacle also has an eye tracker which can determine the viewing direction of the eye. This is because the at least one sensor can determine the brightness of the visible light which is incident upon it from the viewing direction of the eye determined by the eye tracker. And the control loop may take the brightness measured by the sensor in the viewing direction of the eye as the actual value. This clearly leads to a very exact suppression of the actual glare.

It is of particular interest for safety applications if either the light source or an additional second light source is suitable for the dazzling of a living being, an optical sensor or a camera. For example, the light source might be suitable to dazzle a night vision device, which may already 25 be achieved with low intensities, e.g. from an infra-red light source. Military night vision systems no longer function with increasing brightness, because the very sensitive receiver/residual light amplifiers are "exceeded" as of a certain brightness, i.e. they fail in the event of too much light.

Clearly, a second light source should also only illuminate during the time of the low transmission state of the liquid crystal cell. This opens the possibility of blinding a criminal or opponent without being blinded oneself.

The object is also achieved by a method which corresponds to an operation according to the principles of the described system.

Glare Weapon

The object is further achieved by a system for dazzling a living being, an optical sensor or a camera, comprising:
spectacles for a wearer with at least one eye, with at least one spectacle lens, wherein the at least one spectacle lens comprises a liquid crystal cell, the transmission of which may be varied by a suitable control. The liquid crystal cell is so designed that the transmission of the liquid crystal cell may be switched between states of high and low transmission. In addition, there are means for controlling the time of the state of high transmission of the liquid crystal cell.
further, the system has a light source for dazzling a living being, an optical sensor, or a camera that illuminates during the low transmission state of the liquid crystal cell.

The great advantage of such a system is that by means of the light source, a criminal or an opponent, for example, may be blinded, but the wearer of the spectacles is not dazzled because the light source only illuminates when the liquid crystal cell in the spectacles blocks the light.

In addition, the blinded or to be blinded system may be behind a specular screen (e.g. in a vehicle), or randomly reflecting objects, or may intentionally use a mirror to deliberately return the glare back to the transmitter. According to the current state of the art, the operator of the glare weapon is then unprotected and could be impaired by their own light via the reflection. In addition, team members of the same task force, on the right or left of the operator, could also be blinded by reflections according to the current state of the art. This also applies to the careless and inadvertent handling of glare weapons. The proposed system eliminates these risks.

For example, the light source could be suitable to dazzle a night vision device, which may already be achieved with low intensities e.g. from an infrared light source. Military night vision systems no longer function with increasing brightness, since the very sensitive receivers/residual light amplifiers are "over-modulated" at certain brightnesses, i.e. they fail in the event of too much light.

Such glare weapons are often also referred to as "dazzlers", while the use of a laser is also referred to as a "laser dazzler".

If, in security tasks, one does not only want to blind the opponent, but in particular, e.g. on a dark night, wants to illuminate the scene with one's own spotlight for better personal orientation, the problem is that the extremely bright light of the dazzler fades the spotlight's own light so that the spotlight is no longer sufficiently visible in the distance, i.e. in particular the specific blinded person or the blinded system may not be observed sufficiently well with respect to reactive behavioral changes (surrendering, stopping, retreating, changing direction, etc.), or relative to general data collection (reading car license plates, etc.) because of the fading.

Moreover, the fading is often so bright that even the environment of the blinded person or of the blinded system is no longer sufficiently visible when the headlight illuminates the surroundings of the dazzled opponent in order to detect, for example, suspicious changes in the scenery (active monitoring of the environment).

In order to remedy this situation, the system comprises a second light source and means for controlling or regulating the luminance times and the luminous intensity of the second light source so that it shines during the times of the state of high transmission of the liquid crystal cell.

Such a solution allows a user of the system to illuminate a scene for themselves while the opponent remains blinded. The second light source illuminates during the times when the liquid crystal cell transmits the light. The dazzling light source only illuminates at the complementary times when the liquid crystal cell blocks the light. The user of the system is not dazzled by the glare weapons, but may illuminate and explore the scenery using the spotlight.

In a further option, it is conceivable that the second light source is a display. The user of the system may then dazzle an opponent while reading the information from the display of instruments themselves undisturbed.

In order to prevent or at least make it difficult for an opponent to: a) synchronize the lighting times of the glare weapon with a comparable system and, during these times, switch the liquid crystal cell to blocking (scenario A), or even worse, b) whenever the glare weapon is off, the opponent guesses that the spectacles of the transmitter are open, and that they may dazzle it with his own glare weapon in this time slot, and so the control or regulation of the liquid crystal cell and of the light source of the glare weapon may be so designed that the temporal position of the times of the state of high transmission may be continuously or discontinuously changed (phase hopping) within a period of time of the high transmission state and the low transmission state. Alternatively, the duration of a period of high transmission times and low transmission times may be continuously or abruptly changed (frequency hopping). It is then important that these changes are determined by a secret coding key. Any patterns should not be repeated periodically in an easily recognizable manner.

An opponent's self-protection against glare (scenario A) cannot be guaranteed with the coding in the case of sufficiently fast reacting systems (in the sense of technological weapon equality), since the opponent is mainly only guessing the "falling out flank" of the glare weapon* (*=incomplete knowledge/information asymmetry), they cannot shoot with their own (opposing) glare weapon into all open time slots of the spectacles with continuous safety (maximum energy), especially if the pulse patterns are no longer synchronous and complementary via coding, but "jump illogically", i.e. a short dropout at the flare weapon (falling light flank) does not necessarily mean that the spectacles of the transmitter are subsequently open, especially since a 100 Hz system has at least 100 time slots per second, and not everyone has to use this "consistently logically".

In addition, the laser dazzler together with the lamp may produce more than just a hopping "drop out" or "light pulse" per cycle (especially because lasers and LED lamps may now be modulated extremely quickly, e.g. by a factor 100 times faster than the LC shutter=10 kHz instead of 100 Hz. This inevitably leads to deception and confusion of the opponent, especially if not every "dropout" or "light pulse" leads to a synchronous opening of the spectacles. The aforementioned secret coding may also be applied "systemically", because the "publicly transmitted information" (glare weapon dropout or spotlight pulse) then no longer exists in a precise logical connection with the opening times of their own spectacles (or sensor).

The system may be perfectly combined with the systems and methods described below for color coding of the sight of various people.

The object is also achieved by a method which corresponds to an operation according to the principles of the described system.

Own Light Detection

The object is further achieved by a system for the improvement of visibility by glare suppression with spectacles for a wearer with at least one eye. The spectacles have at least one spectacle lens, wherein the at least one spectacle lens has a liquid crystal cell, the transmission of which may be varied by a suitable control. The liquid crystal cell is so designed that the transmission of the liquid crystal cell may be switched between states of high and low transmission.

The system further comprises at least one sensor for measuring the brightness of the visible light incident on the at least one sensor, wherein the at least one sensor is preferably arranged on the side of the spectacle lens facing away from the eye.

In addition, the system comprises a closed-loop control circuit for the control of the transmission of the liquid crystal cell, wherein a setpoint value for the brightness is preset at the eye of the spectacle wearer, and the control circuit takes the brightness measured by the at least one sensor as the actual value. In this case, the regulation or control is so designed that the times of the state of high transmission become shorter with increasing glare.

Finally, the system also includes a light source with means for controlling or regulating the luminance times and the luminous intensity of the light source so that this illuminates during the times of the state of high transmission of the liquid crystal cell. The temporal integral of the product of the luminous intensity of the light source and the transmission of the liquid crystal cell remains constant during a change in the times of the state of high transmission within a predetermined tolerance.

In order to distinguish the cause of the light detected by the at least one sensor, i.e. the question as to whether it is light from extraneous light sources such as a dazzling light source, or light from one's own light source, it is crucial that the at least one sensor detects the brightness of the visible light incident on it only in the times of the low transmission state. This allows the desired distinction, since the measured brightness may then only originate from extraneous light sources.

Such a system prevents dazzling from its own light source.

The system may be perfectly combined with the above-described systems and methods for the suppression of glare with the aid of an eye tracker.

The object is also achieved by a method which corresponds to an operation according to the principles of the described system.

RGB Coding

The object is further achieved by a system for the color identification of objects in the field of view of a plurality of spectacle wearers. The system comprises one pair of spectacles per spectacle wearer, each with at least one eye. The spectacles each have at least one spectacle lens, wherein the respective at least one spectacle lens has a liquid crystal cell, the transmission of which may be varied by a suitable control. The liquid crystal cells are so designed that the transmission of the liquid crystal cells may be switched between states of high and low transmission.

The system comprises means for controlling or regulating the times of the high transmission states of the liquid crystal cells so that the respective liquid crystal cells are set to high transmission states at different times.

In the system, each spectacle carrier has an RGB light source, as well as means for controlling or regulating the luminance times, color and intensity of the RGB light source so that:

the RGB light source for a first spectacle wearer is illuminated with a first color at a time of the state of high transmission ($T_{on}$) of the liquid crystal cells (LC) of their spectacles; and the RGB light source for a second spectacle wearer is illuminated at a time of the state of high transmission ($T_{on}$) of the liquid crystal cells (LC) of the spectacles of the second spectacle wearer with a second color that is different from the first color.

In this way, in group applications with a plurality of persons, a color coding of persons or objects may be carried out in the field of view of the respective participants, which only the individual sees and not the others.

When the RGB light source, e.g. is so designed that it is suitable for producing white light, this light may, for example, be decomposed into a fast temporal sequence of a red, a green and a blue light pulse. If only one of these light pulses falls into a time of the state of high transmission of the liquid crystal cell of a participant, they only see this color. An outsider, in particular someone without shutter spectacles would perceive the light as white.

Members of a group, whose times of the state of high transmission of the liquid crystal cells are synchronized with each other, see the same color. Members of another group with different opening times of the liquid crystal cells see a different color.

For the color coding to remain secret or invisible to a third party or outsiders without spectacles, the colors which are necessary to be transmitted in a time-dependent manner are emitted from the corresponding RGB light sources in the times of the low transmission state of the respective spectacles, in order to leave a white color impression for those not wearing any of the spectacles.

In order to see something of the color markings of other subscribers or groups at least in an attenuated form, the liquid crystal cell of a first spectacle wearer may provide a weakened, but not zero, transmission in a time of the state of the high transmission of a second spectacle wearer.

The color coding may thus take place not only in the three primary colors red, green and blue, but in any color that may be blended from red, green and blue. In order to freely define the color in which the RGB light source for the first spectacle wearer is illuminated in a time of the state of the high transmission of the liquid crystal cell of their spectacles, an arbitrary intensity value between 0% and 100% of a color component of each primary color of the RGB light source may be added in the time of the state of the high transmission of the liquid crystal cell. The up to 100% missing portion is radiated for each of the three primary colors of the RGB light source during the corresponding time of the low transmission state of the liquid crystal cells.

This secret color marking may be perfectly combined with the above mentioned glare weapon.

Furthermore, the system may be perfectly combined with the systems and methods for the suppression of glare with the aid of an eye tracker as described above.

The same applies to the above-described coding with a coding key which would prevent the possibly-used color code from being detected by an opponent.

The system may also be combined with the above-described systems and methods for improving the legibility of display instruments.

The object is further achieved by a method which corresponds to an operation according to the principles of the described system.

Enhancing the Spatial Impression

The object is further achieved by a system for enhancing the spatial impression of an object. The system includes spectacles for a wearer having at least two eyes, a right and a left eye. The spectacles have a spectacle lens in front of each of the two eyes, wherein each spectacle lens has a liquid crystal cell, whose transmission may be varied by a suitable control. The liquid crystal cells are so designed that the transmission of the liquid crystal cells may be respectively switched between states of high and low transmission. The spectacles also have means for controlling or regulating the times of the state of the high transmission of the liquid crystal cells.

Furthermore, the system comprises two light sources which are each assigned to one eye, wherein the stereoscopic base of the light sources is greater than the eye distance. In addition, there are means for controlling or regulating the luminous times of the light sources, wherein the light source associated with the right eye illuminates during a time of the state of the high transmission of the liquid crystal cell of the right eye, while the light source assigned to the left eye does not illuminate and the liquid crystal cell of the left eye is set to the low transmission.

And vice versa.

This method leads to a better 3D perception, which in the technical literature is referred to as "2.5D", since one cannot look completely behind the object. The objects are illuminated from a larger stereoscopic base, and this illumination is respectively perceived by the right and left eye. This results in the apparent optical effect that the pupil distance is as great as the distance between the two light sources, which improves the possibility of depth resolution.

The fact that RGB signals may be emitted separately from each of the two spotlights so that third parties always see white light, while a specific color may be made visible for each of the two eyes in corresponding time-selective $T_{on}$ times through the spectacles, means that the object may, for example, be provided with a complementary color seam (e.g. to the right with a red fringe and to the left with a blue fringe).

Basically, in the following description, one must distinguish between physically-caused spatial projections due to the extended stereoscopic base and so-called visual effects or visual accents which are based purely on human perception, e.g. described by the system theoretical transmission channel of visual perception. (Source: Systemtheorie der visuellen Wahrnehmung by Prof. Dr.-Ing. Gert Hauske, TU Munich, Teubner Verlag, Stuttgart, 1994).

An object that has a complementary color space (e.g. right red, left blue) may be somewhat more prominent in visual perception, especially in the case of remote backgrounds or even no background (object in free landscape).

A further enhancement of the spatial impression, or at least a more differentiated perception against a light background, is obtained when the two light sources are amplitude-modulated with a predetermined frequency which is perceptible by the human eye.

This may be used to achieve various visual perceptions, ranging from a simple visual "flashing highlight" a) in the case of light backgrounds (in-phase and out-of-phase), up to deliberately evoked visual effects that seem to enhance spatiality, such as the Pulfrich effect (in particular, antiphase at night).

The aforementioned flashing (a) has the advantage that a temporal brightness variation of an illuminated object in front of a relatively bright background is perceived as contrast-enhancing or as contour-enhancing during the day or twilight, in particular when one imagines that the two different fringe colors of the object (right red, left blue) flashes alternately. Flashing during the day is always a good way to make slight differences in brightness visible to the perception—especially in the case of the arrangement described here.

Furthermore, especially in twilight or at night, the antiphase flashing (b) as well as other suitable influencing of the transmission channel (the right or the left of the LC darkened rather more, as in the case of "HDR vision", or less light transmitted on a channel), the "perceived run time in the face channel" (see above: Prof. Gert Hauske) of an image or both images, is extended so that a Pulfrich effect may be evoked.

This system may be easily combined with the above-described color coding.

Instead of a complementary color space (right red, left blue), a right-left variation of a particular main color (e.g. red) may be used as explained above in the section "invisible color coding". The right color fringe is bright red and the left fringe appears dark red (or the like) to the user 1 of a team, while the user 2 of a team has the right color fringe of an object light green and the left fringe dark green.

In addition, white light may always be added to the enhancement, since there is already a highlight because of the broader stereoscopic base, in particular in the case of objects in front of a more remote background or an infinite background in the free field.

The system may also be combined with the above-described systems and methods for improving the readability of display instruments and glare suppression with the aid of an eye tracker.

Finally, the system may also be combined with the systems and methods for the spatial separation of backlighting (LIDAR) as described below.

The object is also achieved by a method which corresponds to an operation according to the principles of the described system.

LIDAR

The object is further achieved by means of a system for improving the view of a spatial region to be observed through glare suppression. The system comprises spectacles with at least one spectacle lens, wherein the at least one spectacle lens has a liquid crystal cell, the transmission of which may be varied by a suitable control. The liquid crystal cell is so designed that its transmission may be switched between states of high and low transmission. The system further comprises means for controlling or regulating the times of high transmission of the liquid crystal cell.

The system also includes a pulsed light source that emits light pulses. The light source is so designed that it may generate light pulses whose temporal duration is shorter than that which the light of the light source needs in order to traverse the spatially observable region in the viewing direction of the wearer.

The spectacles further comprise means for controlling or regulating the times of the state of high transmission of the liquid crystal cell, which are capable of so temporally setting the times of the state of high transmission of the liquid crystal cell that only the backscatter signal of the light pulse from the spatial region to be observed Is transmitted by the liquid crystal cell.

In this way, an effect similar to the laser-based measurement method known as LIDAR (Light Detection And Ranging) is achieved. The spectacle wearer sees the backlight only from the spatial region that has been cut out by the control of the spectacles. In this way, the usual scattered light resulting from fog, snowflakes or rain drops, which are directly in front of the headlight, e.g. of a car, is avoided.

In order to increase the switching time of the liquid crystal cell, it is advisable under certain circumstances to reduce the area of the liquid crystal cell. If necessary, a transition from a simple spectacle lens to a combination of two collector lenses, in whose focus as small as possible a liquid crystal cell is arranged, is required.

In addition, special liquid crystals may also be used, such as, for example, multiple layers (stacks) of ferroelectric surface-stabilized crystals (FLC) in order to achieve the very fast switching requirements in the time range of the velocity of light.

The system may be perfectly combined with the above-mentioned systems and methods for the suppression of glare, as well as the steadily readable display.

The same applies to the amplification of the spatial view. This may help to increase safety when driving.

The object is also achieved by a method which corresponds to an operation according to the principles of the described system.

Further details and features will become apparent from the following description of preferred exemplary embodiments in conjunction with the subclaims. In this case, the respective features may be implemented in themselves or as a plurality in combination with one another. The possibilities for solving the problem are not limited to the exemplary embodiments. Thus, for example, range data encompass all intermediate values (not mentioned) and all conceivable subintervals.

Intelligent Spectacles with Eye Tracker

All the above-mentioned problems are solved with "intelligent spectacles" consisting of at least one spectacle lens in the form of a liquid crystal cell LC, with a closed-loop real-time PID control circuit, but preferably consisting of two completely independent spectacle lenses and control circuits of the type mentioned. The transmission of the liquid crystal cell may be changed by appropriate control in such a way that it may be switched between high and low transmission states, thereby achieving a shutter effect. If this is done quickly enough, the visual impression of the respective eye may be changed on the basis of the inertia of the visual perception of the human being.

In order for a closed-loop control circuit to be implemented, at least one photosensor must be "on the inside" per eye, in such a way that it is able to see through the shutter in the direction of the eye and thus measure the "actual brightness". This serves as the "actual value" for the control.

Defining comment needs to be made on the above-mentioned actual brightness value measured by the shutter because, depending on the technical facts, a discrete (point-to-point) actual value on the time axis and an integration result must be distinguished over a complete shutter cycle T:

1. In actuality, the photosensors available today may be read out so quickly that light intensities passing through the shutter may be measured on the time axis on a point-by-point basis (e.g. with sampling frequencies in the microsecond range), similar to a digital storage oscilloscope with an optical measuring head, so that a discrete actual value curve may be stored in a volatile memory of the micro-controller. In this process, it is possible to see exactly when the shutter is opened ($T_{on}$, or transparent) within a pulse width modulation (PWM) cycle T and when it is closed ($T_{off}$ or non-transparent). For example, if the shutter system is operating at a fundamental frequency of 100 Hz, the temporal memory depth is $\frac{1}{100}$ Hz=10 ms. At the end of a cycle, the microcontroller may form an integral via this brightness profile purely mathematically and thus supply the "actual value" of a cycle.

2. On the other hand, the same photosensor could also be integrated physically and electronically or with respect to switching technology over the entire cycle T, i.e. over the abovementioned 10 milliseconds, in such a way that precisely at the end of the cycle T, there is a measuring result which is then read by the microcontroller without a mathematical averaging having to be effected. In the present invention, a photosensor is used to measure the actual value, which enables the rapid point-to-point/discrete measurement. In order to avoid misunderstandings, the term "actual value" is generally used in the text when a "gray value" (average brightness passing through cycle T) is converted or integrated via the cycle time T, in particular since the human being likewise only perceives gray values, even when, in reality, only temporal ratios pass from $T_On$ to $T_{Off}$.

The photosensor thus effectively takes over the role of the eye, to measure the "real brightness" that falls on the eye, not just any random external brightness. The eye is used as low pass in an ON-OFF keying PWM, in that the gray values are generated only in the eye or only in the human perception, whereas the spectacle lenses in reality never perceive gray values. Strictly speaking, in analogy to the abovementioned integration scenarios for the actual value (1 and 2), a third scenario may be defined by integrating the microcontroller and/or the photosensor until a gray value is reached, which may also be perceived by humans as a gray value (e.g. after integration over about 250 to 500 milliseconds). If this perceptible actual value is meant, this is usually indicated separately in the text.

The photosensor or brightness sensor is at a certain distance (typically 1-3 mm) from the LC cell, so that the LC area actually considered, is larger than the chip area of the sensor due to its opening angle. This results in a better averaging of the brightness and a more accurate/stable measurement in the case of point "LC domain formation", or in the case of point contamination on the opposite side of the LC cell. In any case, for safety reasons and for thermal reasons, it is appropriate to provide an outer protective glass, which also constitutes the outer design of the spectacles, at a distance of 1-3 mm in front of the LC cell. Thus, such point contamination (small flies, dust particles, etc.) will no longer have any influence on the LC and certainly no influence on the photosensor. In addition, the internal photosensors (if they are conventional, and thus non-transparent, photosensors) are applied in the outer LC edge region or spectacle frame region so that they do not interfere with the field of view.

However, in order to be able to determine the actual brightness value in the center of the LC shutter or, as accurately as possible, at least two, preferably three, photosensors per eye are used in the statistical center of the pupil in the case of straight-ahead vision. For example, they may be arranged in a triangle, on the corner of which the statistical local mean value of the pupil comes to lie, which is usually identical (i.e. with non-squinting humans) with the point of the straight-ahead view. With the help of a triangulation calculation, the average brightness with respect to this static local mean value or the straight-forward view may then be calculated and 10 used as the "actual value" for the control.

In addition, a plurality of internal photosensors per eye have the advantage that as a result of this redundancy, the measurement reliability is maintained, even in the event of contamination or in the event of a strong punctual light incidence (e.g. random light reflection on only one of three photosensors).

A "setpoint" is required for the control, which is initially preset by means of a type of potentiometer or similar "adjuster" in such a way that the eye remains constantly adapted to the dark, similar to a relatively strong pair of sunglasses, e.g. with protection level III (S3, 8-18% transmission).

The control circuit must be so fast that the control process can no longer be perceived by the human eye, so that the brightness arriving at the eye is always constant (with respect to the setpoint value), no matter how the brightness changes outside.

This is a so-called real-time control loop, wherein the so-called delta (control deviation), i.e. the difference between the setpoint value and the actual value, is always zero in the retracted state (correct PID parameterization).

Such a control, however, only works if the spectacles are absolutely light-tight with respect to light from the outside. The spectacle case is therefore similar to diving goggles, ski goggles or close-fitting safety goggles with soft dust and light-tight eyecups in the style of swimming goggles or large goggles with wide sidebars and protection against light above and below. With the help of an electrical potentiometer or similar adjuster, the pupil of the wearer of the spectacles a) may 30 slowly open, even "turn" upright until it is 75% above the normal diameter in daylight; and b) remain steadily at this diameter due to the real-time control, so that it is quasi "gently restrained", no matter how the brightness outside may change.

This is done separately for each eye, although in the start-up routine, each eye may be set to the same setpoint value (for example, 100 lx for the right (R) and left (L) eyes). In practice, the setpoint values R and L are comparatively slowly changed (e.g. 2 to 100 times slower than the brightness control), and are also deliberately impacted with slight differences (e.g. 10% more transparency on the left and 10% less transparency on the right). The reasons are explained below.

At least one external sensor per eye (OL, OR) detects roughly and comparatively slowly (for example within 1-2 seconds) the daylight situation in a temporal average and determines whether it is a bright day, a covered day or an indoor environment. This is necessary because the dynamic scope during the day covers a range of 100 lx to 100,000 lx, i.e. a factor of 10,000, while a simple LC cell comprises only a factor of 1000 to 5000 (contrast ratio). The "operating point" of the LC cell is shifted into the correct range during a start-up routine when it is switched on (e.g. on a very bright day of an initial 100 lx at the eye to 300 lx at the eye) by means of a variable setpoint value, which is determined by the external sensor (light day, covered day, . . . ).

This setpoint value, which is initiated by the outside sensor, is also quickly and dynamically changed when the controller is at the lower or upper stop, i.e. the control deviation may no longer be zero because the control variable on the LC cell or the transmission has reached a no longer increasing value (i.e. all the way up or down).

This should not usually be the case, since it is intended to keep the eye permanently adapted to the dark. If the lighting situation completely changes, however, and taking into account the electronically stored empirical values as well as information from the external and internal sensors, shortly before reaching the controller stop in a specific direction (LC fully on or completely off), the setpoint value is so changed that the controller remains in the "control mode"

and does not actually reach this stop, i.e. its response is logarithmic or similarly nonlinear in the widest sense, but allows a gentle and controlled closing of the iris due to the increased transmitted brightness (e.g. when looking directly into the sun). However, this adjustment of the setpoint value for the expansion of the dynamic scope should only occur in rare exceptional cases; In normal operation, the pupil is set to a relatively fixed dark value (e.g. 75% above normal diameter) so that the eye already adapted to the dark is immediately available (i.e. within a millisecond) upon entry into a dark room.

In addition, the two setpoint values (L and R) may have slight differences, e.g. 5% to 30% more transparency on the left than the right, so that the brain may again form an image with a higher contrast range (dynamic range) from the two slightly different images in the perception (known from photography as HDR="high dynamic range", wherein two differently exposed photos are copied into each other). The prerequisite is that the contrast difference does not become too extreme, i.e. it remains imperceptible to humans, e.g. 1% to 60%, preferably 5% to 30%. Higher values >30% are also not excluded, but these are then displayed for a shorter time, so that the brain may nevertheless imperceptibly construct a new image with a higher contrast range. Thus, human perception is affected by using intelligent software algorithms.

In addition, inclination and acceleration sensors may also be integrated in the spectacles, as is customary in so-called "wearable technology" and smartphones, so that e.g. during rapid travel such brightness differences may be automatically reduced or even switched off, in order to avoid, for example, unwanted effects (e.g. Pulfrich effect or other perceptual artifacts).

The highest and most complex form of this type of electronic control is the consideration of right-left contra-lateral pupillary affinity in a "Swinging Flashlight Test" (SWIFT)-like illumination situation, which is effected physiologically via the crossing left-right nerve signal exchange in the chiasma opticum and in subsequent parts of the brain. Specifically, this means that no neuronal stimuli are exchanged cross-wise in the case of a healthy human being without asymmetries in the contra-lateral pupillary affinity (as for example in the case of the relative afferent pupil defect RAPD) in exactly the same electronic setpoint values for both eyes (L=R=const.), since the brightness is always constant on both eyes. There are three ways to exploit this effect:

1) An increased control signal (e.g. intensified darkening) on one channel (L or R), with identical nominal values (R=L=const.), signals an asymmetrical illumination situation, e.g. excessive outdoor light on the relevant channel. The microcontroller of this channel communicates with the other microcontroller or the state machine of the other channel the nearly-reaching or overshooting of the channel of the under-illuminated side may then open.
2) Intentional operation in the HDR difference mode may lead to a channel that is switched brighter (more transparent), in particular if it is switched too fast and too circumferentially transparent (delta t, delta T relatively high), a contra-lateral pupil contraction on the other channel. In order to take into account this effect (to compensate=negative feedback, or, if necessary, to amplify it=positive feedback), the other channel is gently and appropriately controlled in such a way that there is an improved view for the other eye, but without it leading to a new contralateral transfer to the originally influenced channel. For this purpose, attenuation is provided in order to prevent the system from being scanned by both pupils and both software-controlled channels. The external light situation, the working points of the two controllers, the transient/illumination changes on the respective channels (for example bright day, cloudy day, proximity to the control stop) and the difference between the controllers are taken into account.
3) Medical and psychopathological indications:
  (a) For patients with a relative afferent pupillary defect (RAPD), the right-left pupil behavior pattern of the patient may be stored in the software of the microcontroller, so that during operation within the two above-mentioned modes (1 and 2) correct LC transparency is taken into account in such a way that the perceived brightness is always constant or corresponds to certain desired values.
  b) For patients with medically-prescribed right-left visual training (for example, after a stroke), one side may be alternately darker or lighter depending on certain temporal patterns.
  (c) For emergency service personnel in stressful situations (e.g. soldiers in action), who have an acutely increased adrenaline level and therefore generally dilated pupils, the software may reduce the transmission accordingly by slightly decreasing (slightly darkening) upon instruction (key), wherein the visual perception is more pleasant in brightness.

The inside photo cells are at least doubled or even tripled. This serves not only to calculate the average brightness in the most likely location of the pupil (as described above), but also for safety reasons. For example, the software can recognize a contamination or a defect of a certain photo-sensor by logical comparison (for example, two sensors show similar brightness and only one shows no brightness at all), and as a consequence only take into account the two photosensors that are functioning.

For this purpose, the software contains, in addition to the permanently calculating controller components, purely logic safety routines (separate state machines), which ensure the functioning of the spectacles constantly in parallel to the controller. (In this context, it should be noted that the most fault-tolerant spectacles of this type, which are intended for automotive applications, are dual-core or tri-core processors approved according to the ASIL standard, which test both hardware and software for errors.

Eye Tracker of the Simple Type

In analogy to the above-mentioned photosensors or camera types which simulate a human eye, a second sensor to observe the eye, is placed inside the spectacles, where this sensor is located. This could e.g. be mounted on the rear side of the aforesaid sensor or slightly offset therefrom. Various types of sensors may be employed, e.g. relatively simple and inexpensive photosensors, or CCD sensors, or higher-resolution imaging systems. In the simplest case, the viewing direction is only roughly detected. In particular, the left-right movement of the eye may easily be detected even in the white part of the eye (sclera) by using a coded infrared light barrier. Infrared light is not perceived by the eye, but is reflected differently depending on the viewing direction. A coding of the IR source is necessary so that there is no confusion with other light sources and reflections on the receiver side. This encoding may be cyclic in the simplest case (e.g. 10 kHz rectangle with known frequency and phase position). A phase-sensitive detector (PSD, also known as a boxcar amplifier) may carry out a very accurate amplitude measurement from the frequency and in particular the phase position with respect to the transmitter signal after low-pass integration over approximately 10 cycles, i.e. with approximately 1 kHz, even if this is very weak compared to the "noise" of other IR signals.

This is only one example of a simple eye tracker. The pupil position may also be determined by a very similar method—likewise in reflection, but in this case with respect to the absorption in the dark pupil instead of the reflection on the white sciera. Since reflection photoelectric sensors are very cost-effective, such sensors may be installed both inside at the eye (close to the nose) and outside the eye (close to the temple), possibly under the eye (looking up/down)—thus 2 to 3 sensors in total. Several such sensors increase the measuring accuracy with respect to the viewing direction.

However, an eye tracker is ideally used when it uses a tiny high-resolution imaging camera similar to that used in smartphones or notebooks. This camera detects the pupil position with respect to the viewing direction and thus of all angles.

Correlation Calculation from Photosensors and an Eye Tracker

The directional and brightness information of the photocells/cameras are correlated mathematically with the direction of the eye determined by the eye tracker. This means, for example, that the viewing direction is initially taken as the output value, while the incident brightness is measured simultaneously (i.e. in real-time) at the exact same angle and is constantly regulated. Since this is a real-time PID control loop, wherein the control deviation is always zero, the brightness in the viewing direction will always be constant—namely, the adjusted setpoint value.

If this control functions very precisely, which is possible using high technology, the pupil on the main axis never experiences a difference in brightness. This control mode may be selected according to the application (e.g., sports, automotive, industry, medicine, military), e.g. by a switch or other command (e.g. via a smartphone connected to the spectacles via Bluetooth or the like).

On the other hand, this extremely fast and precise control mode could also lead to undesirable artifacts in the perception depending on the application. Therefore, an alternative mode may be set, wherein the software is deliberately slowed down or the brightness is adjusted only in slight angle gradations. For example, only when the user really looks exactly into a laterally located source of glare (e.g. car traffic) would it be immediately adjusted to constant brightness, otherwise, when the pupil moves back and forth only slightly in the middle and out of the region of no backlight, this is constantly regulated to this brightness.

In addition, the individual and age-dependent glare sensitivity function, which may be stored in the software as a formula or look-up table (LUT), may be stored as a template (e.g. with multiplicative weighting) via the signal of the forward-looking brightness sensor. Although this sensor does not move like an eyeball, but is rigidly mounted to be straight, this template is moved along with the eye tracker signal according to the eyeball movement. This practically creates an artificial eye, which takes into account the individual viewing angle-dependent glare sensitivity, which is used as the reference variable (also referred to as the "actual value") in the real-time PID control circuit. It is left to the person skilled in the art to make the algorithms gentler or stronger depending on the intended application. Alternatively, provision may be made for the user to make a selection.

General System for Glare Suppression

This is a system for visibility enhancement by means of glare suppression (also known as the anti-glare system), which implements intelligent and safety-relevant multi-channel real-time controls for visual enhancement, wherein the left and right eye are treated separately and/or comprise several users for group applications.

In order to achieve a consistent overall system wherein the visor and the spotlights continuously and analogously interact in such a way that an application range from zero darkness (0 lux) to twilight (e.g. 100 lux) is seamlessly covered, For example, in the case of constant integral brightness of the spotlights, spectacles controlled in real time to constant brightness, as described above, are needed, while, in many cases, a somewhat simplified version (without an eye tracker) is sufficient. Such spectacles allow the suppression of glare by constant control to a brightness value. In addition, the eye is permanently kept quite dark (i.e. a relatively large pupil is adjusted) so that the user is immediately and imperceptibly adapted to the dark (in real time) when traversing a light-dark jump (e.g. entering a dense forest), which otherwise usually takes up to a minute or more. However, it is problematic that the contrast range or the quotient of useful signal and interference signal decreases with increasing darkening through the spectacle lenses (i.e. increasing brightness outside).

In order to correct this, a synchronously operated spotlight is still required (which therefore operates with the same frequency as the spectacles). In this case, the pulse energy should remain largely constant per transmitted light pulse. For this purpose, the temporal integral of the product of the luminous intensity of the spotlight and its luminous duration is kept as constant as possible during a cycle.

System for Glare Suppression with a Display

Hitherto, the use and application of anti-glare systems has mainly been in motorized movement (cars, motorcycles, trains, etc.) or in the case of fast movements under one's own power (bicycles etc.), wherein glare is primarily caused by the headlights of opposing vehicles or by the sun or other disturbing light sources. In such scenarios, it is assumed that the interfering signal (for example, oncoming traffic or the sun) and the useful signal (own headlights) come from completely different directions (sun in the distance, headlights on the car). A somewhat different situation arises when the spurious signal (sun) is reflected precisely at the point where a useful signal is generated, e.g. on a reflective screen surface.

However, both situations have in common that the sum signal at the eye always consists of an interference signal and a useful signal. With respect to the spectacles-eye combination, therefore, nothing changes physically since, from a human perception point of view, a useful signal is always distinguished from an interference signal by time division, while the integral ratio of useful signal to interference signal should be improved. In addition, in both cases, the interference signal may also come from a different direction than the viewing direction of the user, but such an interference signal may also dazzle so strongly that visibility at the viewing point is impaired.

Display systems include all types of screens, displays (PC, notebook, smart-phone, TV, . . . ), fittings, or other visual human-machine interfaces, e.g. cockpit fittings of all types, e.g. In the car, airplane, ship, motorcycle, etc., or other self-illuminating display panels, warning signs, tachometers, clocks, geo-coordinate navigation systems, head-up displays, etc.

This is remedied by modulating the indicator light as if it were the above-mentioned own headlight. This means that whenever the liquid crystal cell of the spectacles is opened in a short time slot (e.g. for only 5% of the cycle time T), the background illumination of the display is switched on briefly and pulse-like, preferably with higher light intensity than normal.

The preset value of the brightness of the display, which is required for a user to read the information displayed on the display, results, on the one hand, from the brightness to which the spectacles control the light striking the eye, e.g. 400 lx, and, on the other hand, from the usual brightness of this display. Since the spectacles are typically controlled to 400 lx, i.e. a rather dark state, the value to be achieved by the product of $T_{on}$ and the brightness of the display is generally below the normal brightness setting of the display. This leaves room for the required pulse-like elevation. This is always problem-free if the background lighting consists of fast-reacting light sources (e.g. white light or RGB LEDs), which in turn may be controlled by a) software or b) an OEM hardware solution.

a) In the simplest case, a software downloaded from the Internet (e.g. an app) may already
so adjust the brightness display backlighting of a smartphone or similar device, e.g. tablet or notebook or a head-up display located outside of the spectacles, that the above-described anti-glare system is implemented.
b) Otherwise, smartphone and tablet devices may be expected to adapt to such a system in the medium term (i.e. already after a few years), by incorporating special overpowered backlighting into their devices. As new consumer terminals appear on the
market, this possibility may, in any event, be regarded as realistic. And in the case of special displays for non-consumer devices (aircraft cockpit, etc.), it is already obvious how such special systems may be easily incorporated into the next generation of indicators through co-operation.

Through such a system, e.g. over 95% of the glare is suppressed, while the light pulses of the screen fall exactly into the open time slot of the spectacles and thus onto the eye adapted to the dark. As a result, the displayed information is clearly visible despite considerable solar radiation (or other disturbing radiation), while the display would not be readable without such a system.

System for Glare Suppression in the Case of Glare Weapons

DEFINITION

The word "glare weapon" or "dazzler" is generally used here to serve only as a generic term, i.e. it is irrelevant to which light-technical implementation (lamp, laser, etc.), wavelength or intensity it refers, so that it equally covers a LASER dazzler with a very high beam intensity or a LASER with variable wavelength (multicolor) or other high-intensity light sources—also in the edge ranges of infrared (IR) or ultraviolet (UV). Common to all glare weapons is the idea of explicitly aggressive tactical glare and interference from opponents (whether as an individual or a group), 5 or to the glare and interference of optoelectronic systems used by the enemy (e.g. sensor systems on tanks or the like).

According to the latest state of the art, the extremely bright light of one's own glare weapon exceeds its own headlight light, so that it is no longer sufficiently recognizable in the distance, even if the surroundings of the dazzled opponent is illuminated with the headlight(s) in order, for example, to detect suspicious changes in the scenery (beyond the already successfully dazzled, so-called active environmental observation).

The present glare suppression system may be combined with such a glare weapon (dazzler). In this embodiment, an anti-cyclic or inverted switching-on signal is fed to the glare weapon with respect to the opening duration $T_{on}$ of the spectacles. The glare weapon is thus always switched off only for the very short time slot (for example, 5% of the cw duration period of the dazzler), in which the search headlamp is switched on, and the spectacles are synchronously open for too short a time. As soon as the glasses close again (non-transparent switching), the glare weapon operates again. This allows a separate two-channel operation (headlight and dazzler) as a whole.

If the dazzler is switched off completely in the short open time slots of the spectacles, this may have disadvantages, since it is then no longer visually traceable. Therefore, for these times, the dazzler may be set to a freely adjustable low luminous intensity of, for example, 0.5-5% of its maximum intensity so that it remains clearly visible to the user and is not inadvertently so strongly suppressed that it is no longer sufficient to know where the glare weapon is shining.

With such a two-channel or even multi-channel operation, consisting of an individual source of own light and at least one individual glare weapon, it is possible to dazzle enemy personnel or their optical equipment (e.g. sensors on a tank), but also simultaneously to illuminate/explore the surrounding environment in the viewing direction with one's own separate light source.

In combination with the embodiments of the system according to the invention described below, it is even possible to mark enemy targets for members of a team (and only for them) in color and to operate the system in an encrypted manner.

System for Glare Suppression with Coding

In particular, a group application is foreseen for use with authorities and organizations with security tasks (BOS) or with the military. This must ensure that the actors do not inadvertently dazzle each other. For this purpose, the components of the system are synchronized with one another. As it can not be ruled out that there are external users of similar systems (whether they are opponents or other teams with a similar task), it is planned to modulate the components of the system (e.g. spectacles and light sources) in such a way that the correspondingly synchronous short opening times of the spectacles no longer correspond to a cyclic or periodic pattern, but their temporal sequence constantly changes according to a secret coding key. In principle this change may take place with regard to all conceivable free modulation parameters, but preferably with respect to their phase position, pulse position (phase and pulse position hopping), frequency (frequency-hopping), amplitude (AM) or combinations of these modulation methods.

Such coding may, of course, also be applied to the above-described configuration of the system with glare weapons. In such a case, the glare weapon also "jumps" back and forth with the secret coded time slots of the spectacles and the own light source on the time axis—only inverted in each case.

It is also conceivable that graduations of coding keys, e.g. one or more additional glare weapons (dazzlers) could be encrypted separately by means of a sub-key (possibly inherited from the team key) per person or per team without dazzling each other by mistake.

The exemplary embodiments are schematically illustrated in the figures. Identical reference numerals in the individual figures denote the same or functionally equivalent elements or corresponding elements with respect to their functions:

Figure 1:
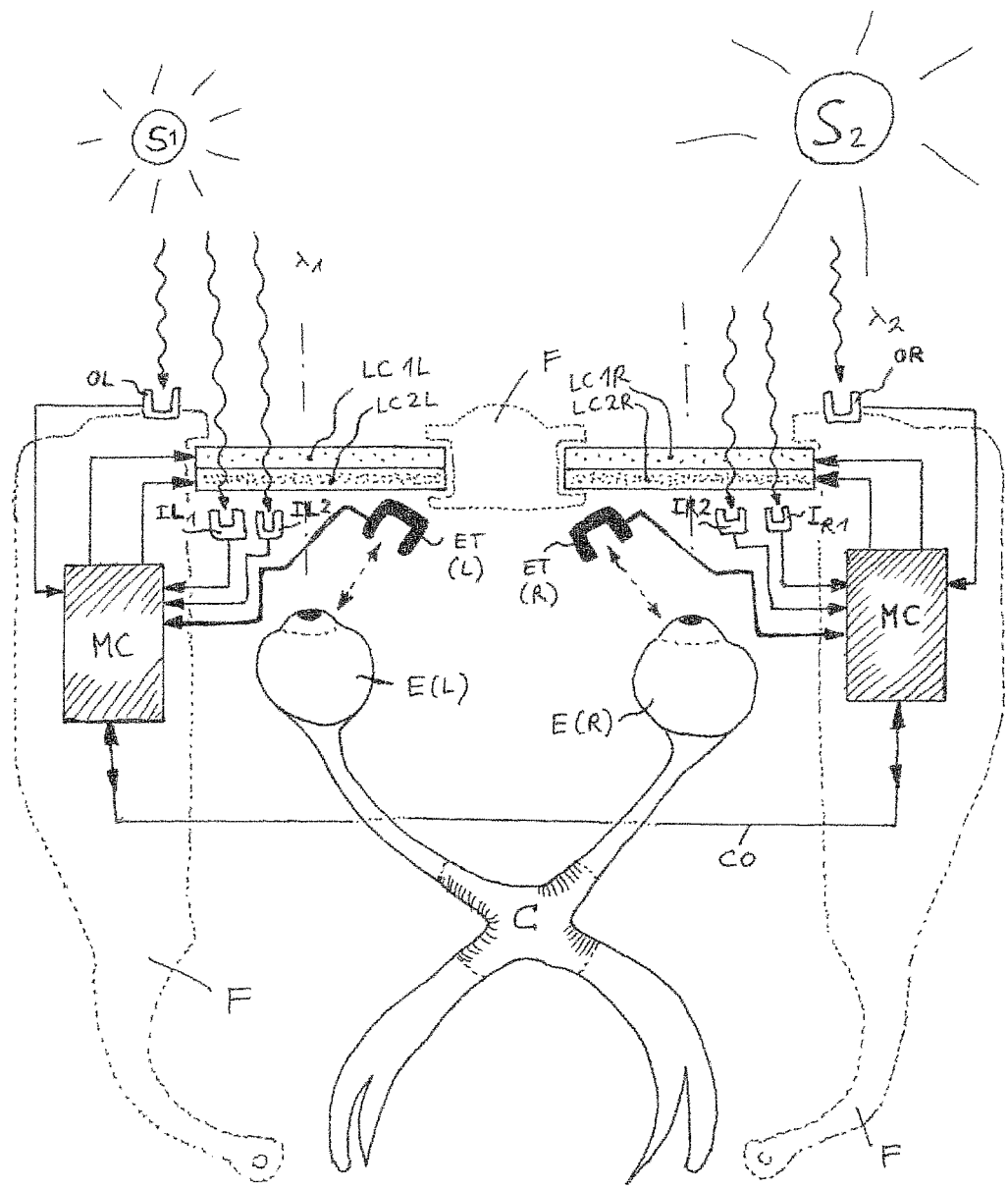
FIG. 1 shows a schematic representation in a sectional top view of the electronic spectacles.

In the following, reference is made in part to FIG. 1.

Everything that follows always applies to one eye (right or left, also referred to as a "channel"). A channel consists of at least one LC cell (but it is also possible to connect two or more LC cells in series) which, depending on the application, contains suitable fast and high-contrast LC material (TN, STN, Fe-LC).

Cells that are more distant from the human body are referred to as "distal", while those closer to the eye are referred to as "proximal." One to three complex photosensors IL1, IR1 are located at a certain distance (typically 1-3 mm) behind the proximal cell, to detect the light incident through the LC cell LC 1L, LC 2L, LC 1R, LC 2R in the viewing direction, wherein a single photosensor consists, in turn, of at least three sensors which span an orthogonal x-y-z coordinate system—wherein the vector (1,1,1) appropriately points in the viewing direction.

As an alternative to such an x-y-z photosensor, it is possible to use a photosensor array which, like a compound eye, comprises significantly more than 3 orthogonal channels. Each channel may measure the brightness over a wide dynamic range so that a "coarse image" is transmitted to the microprocessor.

As an alternative to such a "coarse image", a system (camera) with a significantly higher resolution (e.g. 5 megapixel camera) with an identical miniature size not exceeding a few square millimeters, may be provided with a significantly higher resolution, similar to those already used in smartphones and notebooks. The image transmitted by such cameras to the processor is finely resolved: the dynamic scope and the linearity to measure the brightness are ensured by using highly dynamic chip materials, similar to those used in analytical medical photography.

For pure safety reasons, at least 3 such complex photosensors (x-y-z, or compounds or camera) are used per eye E(L), E(R) (channel).

All of the above-mentioned photosensors may be e.g. in the form of photodiodes, phototransistors, photocells, etc., wherein all of these have in common that they react color-neutrally by including the color-sensitivity curve of the eye (the so-called V-lambda function according to DIN 5031). Photocells of this type are used, for example, in photography for color-neutral illumination measurement. Depending on the ambient brightness (measured by an external sensor OL, OR, or derived from the manipulated variable and setpoint value of the controller MC), a look-up table (LUT) mainly in the case of darkness, may be included in the calculation algorithm, which comprises the V' values for night vision, so that the so-called Purkinje effect (increased blue sensitivity at night) is taken into account. Furthermore, individual, age-dependent glare sensitivity may be taken into account—on the basis of empirical studies, in particular angle-dependent and age-dependent (e.g. Adrian and Bhanji 1991 Illumination Engineering Society of North America).

Free-Form Lens/Channel or Software with Camera

The physical conversion of the above-mentioned eye sensitivity formula may be used for the direction-sensitive measurement of brightness through a free-form lens of transparent material (e.g. glass, plastic, liquid, etc.), which is mounted in front of a photosensor in such a way that it acts like the human eye. It thus creates an "artificial eye", which is as sensitive to glare via the incidence angle as a human eye. Two factors must be taken into account here: 1. the V-Lambda and V'-Lambda functions (Purkinje effect at night); 2. the angle-dependent glare sensitivity.

Instead of this lens, it is also possible to use a black channel (i.e. essentially a bore), which is shaped appropriately by means of a free-form calculation, at the end of which the photoelectric cell is located, so that it receives an opening angle which corresponds to the sensitivity of the human eye.

Alternatively, the formula for glare sensitivity may be implemented purely as an algorithm or in the software, which also receives the high-resolution/high-dynamic image of the camera, since the directional information and brightness per pixel is also contained in the camera image. The camera image may then be weighted with individual (age-dependent) evaluation formulas, especially as one may determine their personal age or other individual preferences or medical indications/recommendations regarding glare sensitivity via any human-machine interface (e.g. buttons on the spectacles, USB-PC software interface, smartphone app via (Bluetooth) wireless).

Eye Tracker

The directional and brightness information of the photocells/camera may also be mathematically correlated with the viewing direction, which may be determined by an eye tracker ET(L), ET(R).

The individual and age-dependent glare sensitivity function, which may be stored in the software as a formula or look-up table (LUT), may then be laid over the signal of the forward-looking brightness sensor as a template (e.g. with multiplicative weighting). This sensor is mounted rigidly on the spectacles. However, due to the eye tracker signal, this template is also displaced according to the eyeball movement, wherein the functionality of an artificial eye is achieved that takes into account the individual viewing angle-dependent glare sensitivity.

Pulse Shaping in the LC Cells

There are three possibilities:

1. Both LC cells are cells which are transparent in the voltage-free state in order to allow normal vision in the event of a system or voltage failure.
2. For high-safety applications where there is a permanent risk of glare in the work area (e.g. a LASER laboratory or when arc welding), LC cells may be used which operate in exactly the opposite way, i.e. they are completely dark in the voltage-free state and may only be switched to become transparent by pressing a safety switch or the like.
3. Mixing of cells of the above-mentioned types, i.e. one that is permeable in the voltage-free state, and an impermeable cell. This arrangement may be used to improve the flank slope at both the ascending and falling flanks of an optical pulse, in the sense of a transparent circuit for a fraction of a second in the form of a square pulse on the time axis (rectangle with high flank slope on the optically measuring oscilloscope image). The advantage of this is the reduced noise and other contrast-reducing artifacts (crosstalk) in synchronous applications with ones own source of light or several participants.

Figure 2:
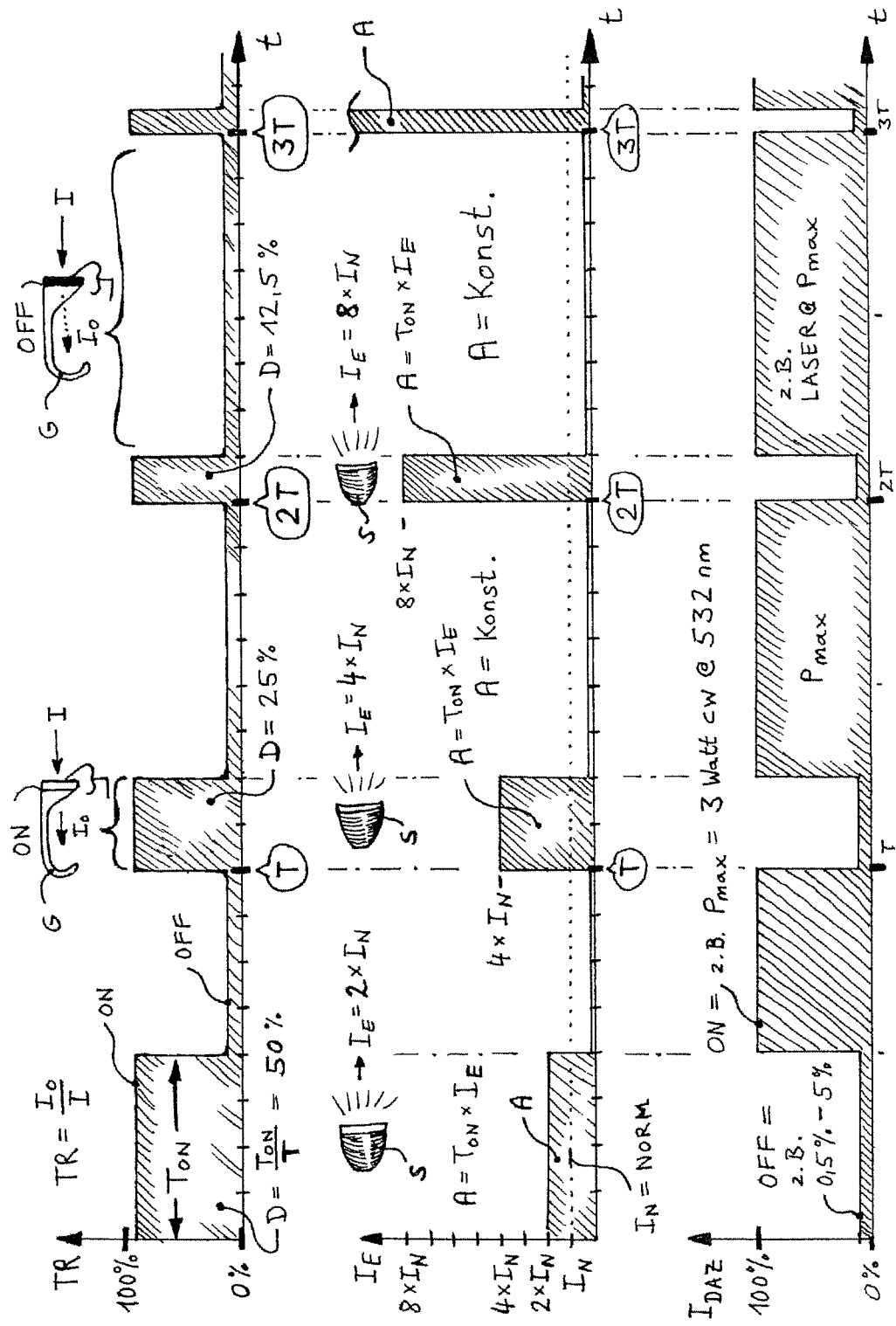
FIG. 2 shows a diagram of the so-called transmission of the spectacles of a glare suppression system over time, wherein the system is equipped with a glare weapon.

The spectacles described above may be used as part of a glare suppression system. FIG. 2 shows the so-called transmission (TR) of such spectacles over time. The transmission is thus the quotient of the intensity $I_0$ passed by the liquid crystal cell LC and the incident intensity I.

The spectacles are opened In the time $T_{on}$, i.e. switched to transparent. In the remaining time (period T minus $T_{on}$), the glasses are closed, i.e. non transparent.

In order to obtain seamless and analog gray values, the signal in FIG. 2 (first line) is implemented as the analog pulse width modulation PWM, i.e. in FIG. 2, for example, only different jump-like states of the PWM are imaged from cycle T to the cycles 2T and 3T. These states may also be written as the percentage pulse-cycle time ratio D (duty cycle).

In order to improve the "SNR" ("Signal to Noise Ratio"), the pulse energy per transmitted light pulse is kept constant within certain limits. In particular, the area A in the middle line of FIG. 2, which results from the active pulse width time $T_{on}$ multiplied by the respective emitted intensity IE (I=intensity, E=emitted) of a pulse, is kept largely constant.

In practice, this may be done by applying a higher voltage or by impressing a higher current in a suitable light source that is designed for such high energies. It is up to the person skilled in the art to ensure that the existing light source is suitable for this purpose.

In addition, the light intensity IE must always correspond to the standardized intensity value I standard, which has already been approved by authorities (TUV, etc.), but multiplied by the reciprocal of a hundredth of the duty cycle D.

EXAMPLE

Pulse-pause ratio=duty cycle=50%=0.5
Reciprocal of 0.5=factor 2
IE=2×I standard

This method is necessary so that the intensity measured over a long time integral always corresponds to a constant I standard. Even if the temporal measurement interval is only 1 second for the authorities, then in the case of a 70 Hz spotlight, so many different pulse heights or pulse cycles will have already been averaged in time so that the required constant light value I standard always results. The principle becomes clear by integrating the signal IE in the middle line of FIG. 2 from t=0 to the cycle end T3.

Moreover, in very narrow time slots in which the spectacles are open and transparent (e.g. 5%), the setpoint value of the control circuit, the eye is so sensitive to light that even small powers of IE (i.e. IE divided by $T_{on}$) are sufficient to achieve a visible improvement of the observed scenery, while about 100–5%=95% of the interfering extraneous light may be suppressed.

The present glare suppression system may be combined with a glare weapon (dazzler). The bottom line of FIG. 2 relates to this situation and shows how the dazzler receives an on/off signal which is anti-cyclic or inverted with respect to the opening time of the spectacles. In addition, it may be seen that the dazzler is limited to a (freely-adjustable) non-zero OFF value of an amount of, e.g. 0.5-5% of its maximum intensity IDAZ may be determined, so that it remains visually readily observable to the user.

Figure 3:
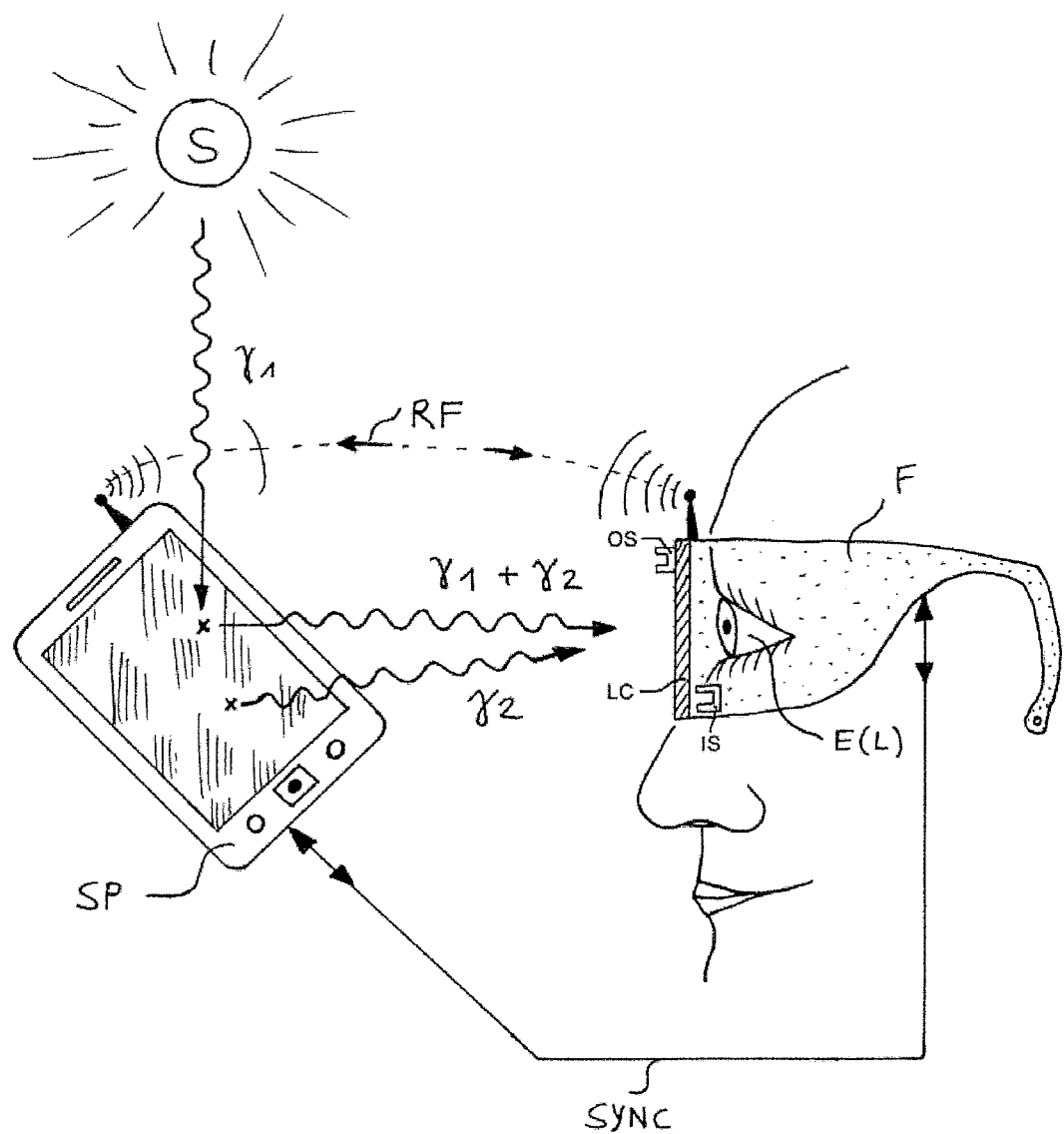
FIG. 3 shows a schematic representation of the situation when a glare signal (sun) is reflected on a indicator or display surface.

FIG. 3 shows how the anti-glare system may be combined with a display to suppress glare by reflection at the display while ensuring the readability of the display. In this case, the sum signal gamma 1+2 at the eye is always composed of an interference signal and a useful signal. In the simplest case, software downloaded from the Internet (e.g. an app) may already have the display backlighting of a smartphone SP or similar device, e.g. tablet or notebook or a head-up display located outside of the spectacles, in such a manner that the above-described anti-glare system is achieved. Over 95% of the sunlight S and gamma 1 may be suppressed in this way, while the light pulses of the screen fall exactly into the open time slots of the spectacles and the eye adapted to the dark.

The synchronization of the spectacles with the display may be effected in various ways:

1) In one case, the electronic device is the "master", which emits simple pulsed light, wherein the spectacles may synchronize purely optically with the help of their light sensors (outside=OS, inside=IS).
2) Optionally, synchronous information may be exchanged via a radio link RF between the spectacles and the terminal. Typically, already existing radio systems, such as, for example, Bluetooth, may be used. The "master" device may remain open here and it is only a question of programming.
3) in addition, sync information SYNC between the terminal and the spectacles may also be transmitted by means of a cable (e.g. USB) or in any other conceivable way. The one that is the "master" of both, may remain open here and it is only a question of programming.

Figure 4:
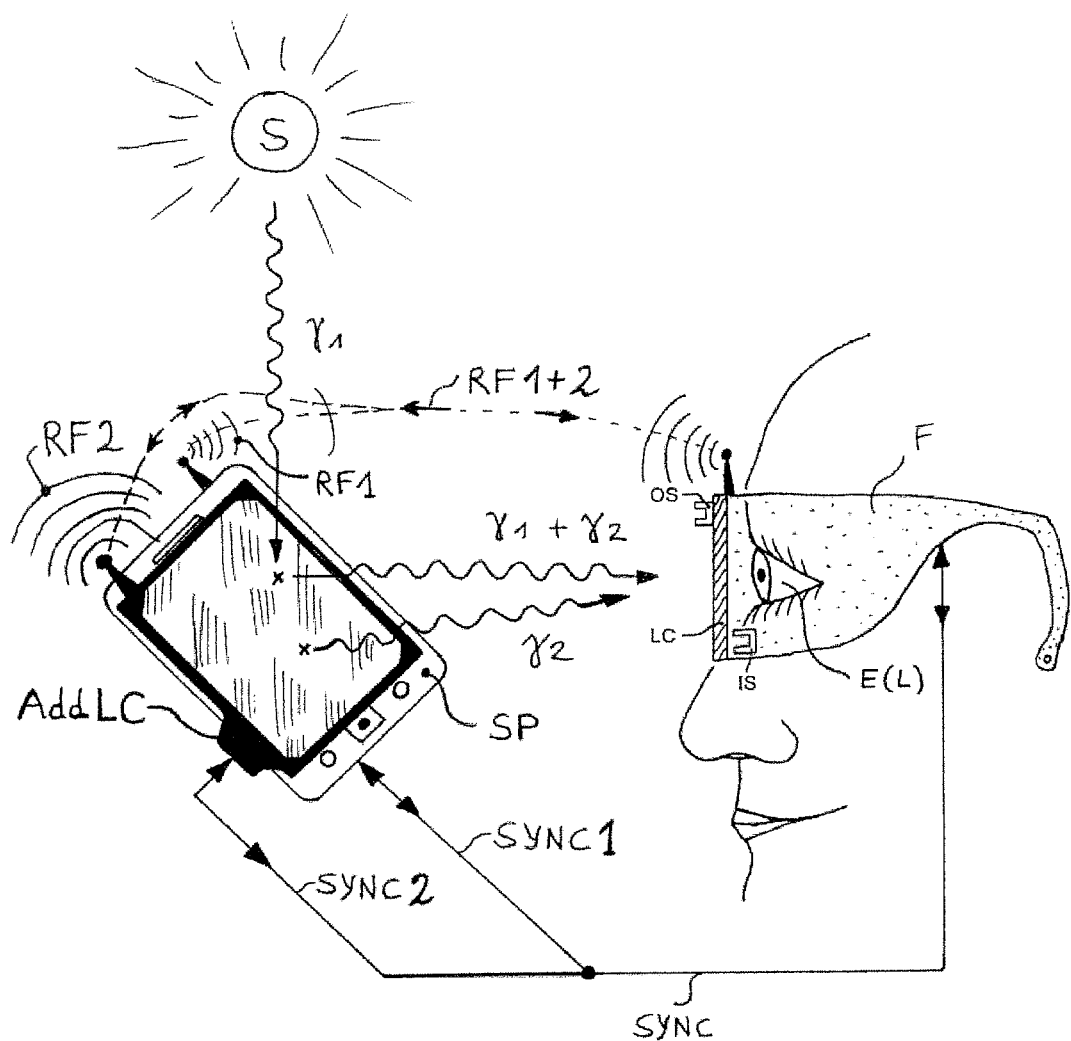
FIG. 4 shows the situation from FIG. 3, with an additional device for non-modulatable displays.

In the following, reference is made to FIG. 4.

A solution is also possible for displays and indicators which do not readily allow the background lighting to be modulated. For displays which have at least uniform background illumination (e.g. paper-like displays with "electronic ink" for reading books), another liquid crystal shutter AddLC may be placed or clamped on this display. This additional shutter modulates the otherwise even (DC), but maximum (or also over-maximal through interference) background light of the display corresponding to the time slots of the spectacles. If the uniform background illumination may be set to very bright, this arrangement results in the already described advantages of glare suppression of extraneous sources of interference S, including the described improvement in legibility. The additional shutter has its own interfaces for synchronization with the spectacles, e.g. Radio RF2 or a cable connector (e.g. USB) or any other access SYNC2.

In addition, a suitable combination of the aforementioned information channels may also be used, e.g. software ("App") for activating the backlighting via radio RF1, and the radio connection RF2 or the cable SYNC2 for synchronization with the spectacles. A purely optical synchronization by the optical sensors OS, IS of the spectacles is also possible.

Figure 5:
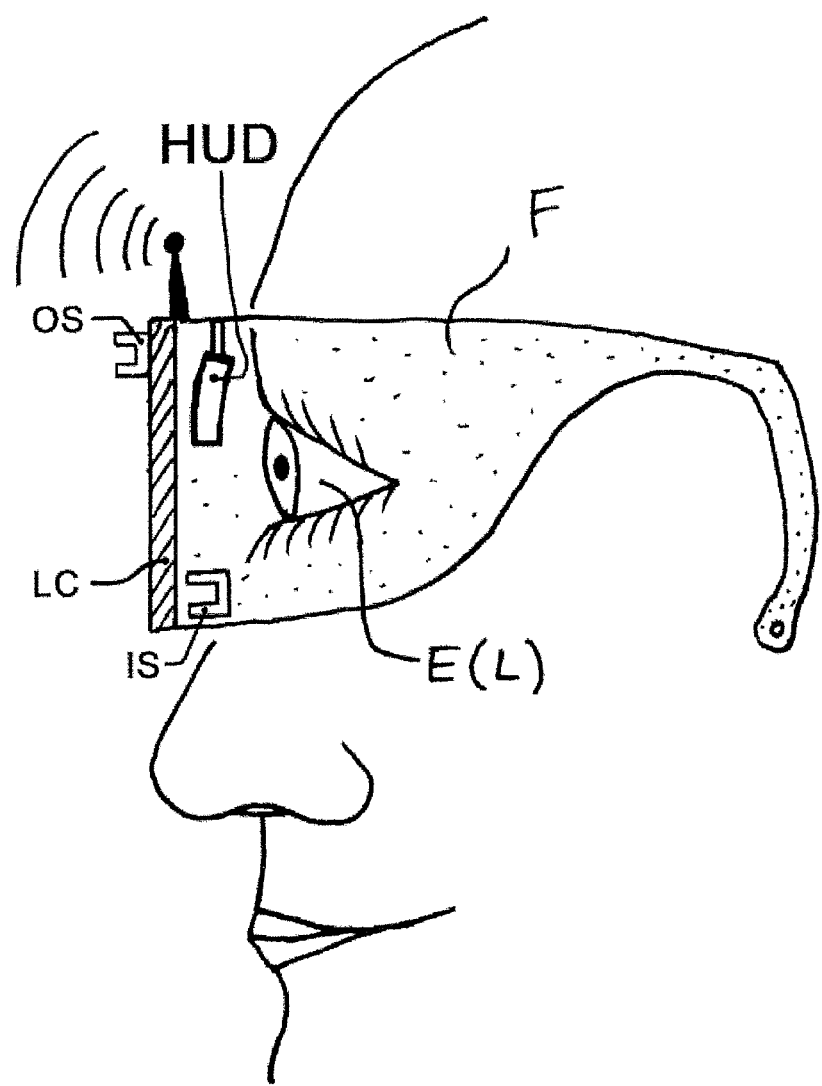
FIG. 5 shows a schematic representation of the situation with a so-called "internal HUD"

In contrast to the head-up display (HUD) external to the spectacles, the "HUD" within the spectacles represents a special case which is shown in FIG. 5 (transparent HUD, similar to "Google Glasses" or Samsung "Gear Glasses" etc.). This results in a read-out improvement through glare suppression, which is important In the event of accidental viewing of the sun (the shutter will be completely or nearly closed at short notice). In addition, an improvement results from the fact that the spectacles always control the exact brightness (largely constant setpoint value) over a very large dynamic range, which in turn ensures the optimum background brightness and/or the optimum contrast, regardless of the internal HUD transparency, however the brightness changes outside. The internal HUD may be read at any time.

Figure 5B:
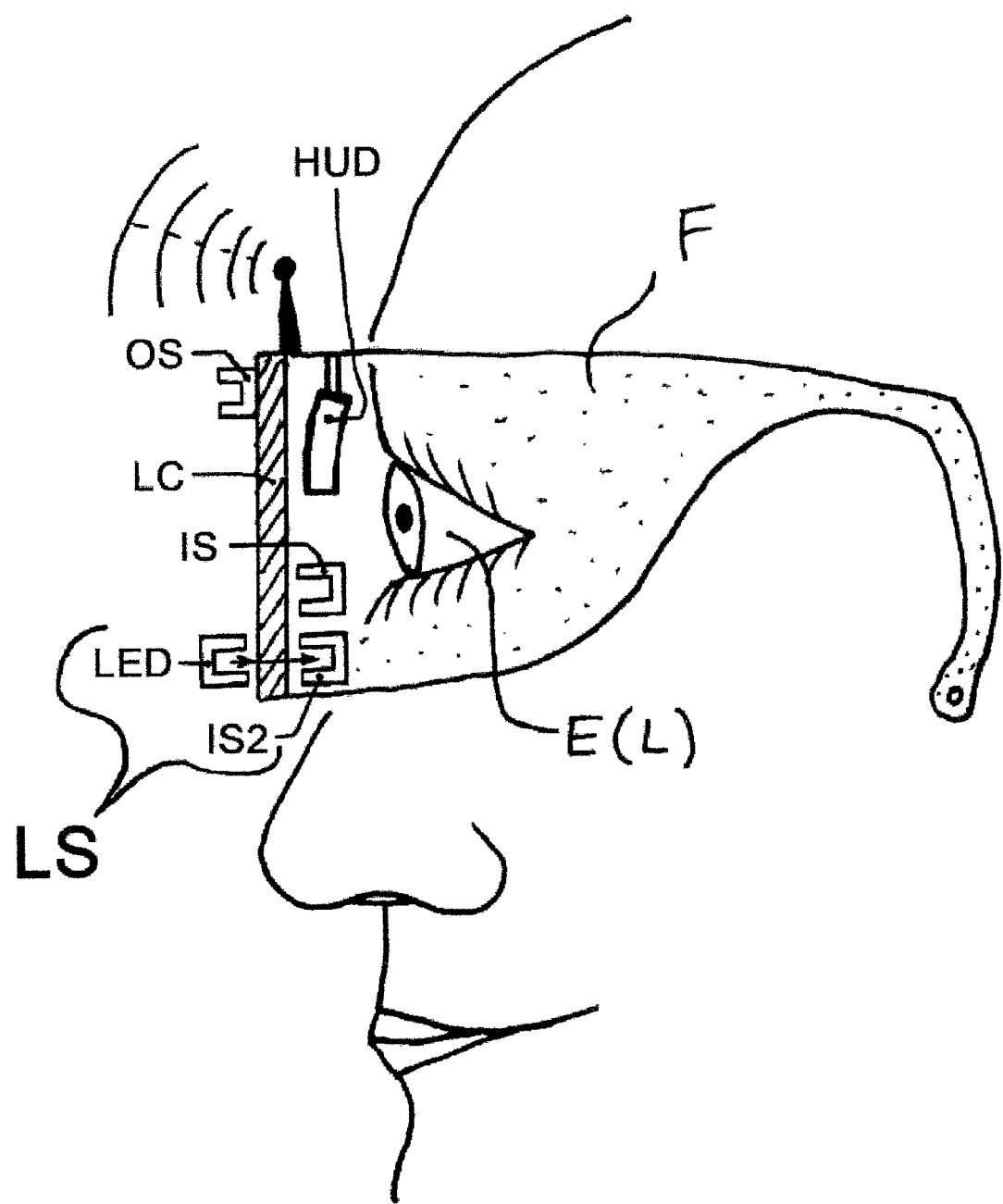
FIG. 5B shows an embodiment as protective goggles for complete darkness, without a source of its own light (working protection)

The following refers to FIG. 5B.

In the context of work protection, there are very simple glare goggles which are worn in the dark, e.g. in research and development laboratories, which have to be dark to carry out the work (e.g. light and LASER experiments, bio-tech), when used by skin doctors during intensive pulsed light therapy (IPL therapy) or the like. However, these protective goggles are often unsuitable for carrying out work because they know only two states, i.e. on and off, and also react incorrectly, since too few photosensors are mounted on the outside, which only control the liquid crystal cells, but not in real-time (see, for example, DE 10 2014 107 587). In addition, the transmission state of the glasses (on or off) remains unknown in the dark, since neither a controller nor a regulator can provide reliable "actual values". Even a regulator would have the problem in complete darkness (e.g. about zero lux) in that the actual value may be too small to provide reliable and safety-relevant information about the correct functioning of the liquid crystal cells.

For such situations, an active light curtain LS is provided for each eyeglass lens (i.e. left and right) comprising an active light-emitting diode LED and a further internal sensor IS2 lying opposite, wherein the transmission through the liquid-crystal cells is specifically transmitted via a wide analog dynamic range and may be measured even in complete darkness.

System for Glare Suppression with Rgb Coding

In the following, reference is made to FIGS. 6 and 7.

Particularly in the case of glare suppression systems provided for group applications for use with authorities and organizations with security tasks (BOS) or with the military, an embodiment may be used which makes it possible, e.g. (for example, for marked targets) to assign a freely selectable light color, which, for example, can only be clearly seen by one team member, and in a weakened form also by his group members, while the light appears white to outsiders.

For this purpose, own light sources are used, which may be modulated not only in their amplitude or luminous intensity, but also in their color (wavelength). In addition to wavelength-tunable light sources such as oscillators (e.g. OPO, OPA lasers, etc.), powerful RGB LASER or RGB LED may be used in the simplest case, wherein they typically have 3 separately controllable channels, namely the so-called primary colors "red, green and blue" according to the RGB color model, which result in a corresponding overlap of white light. Other types and combinations of primary colors close to the RGB color model are also possible as long as they result in total white light.

Figure 6:
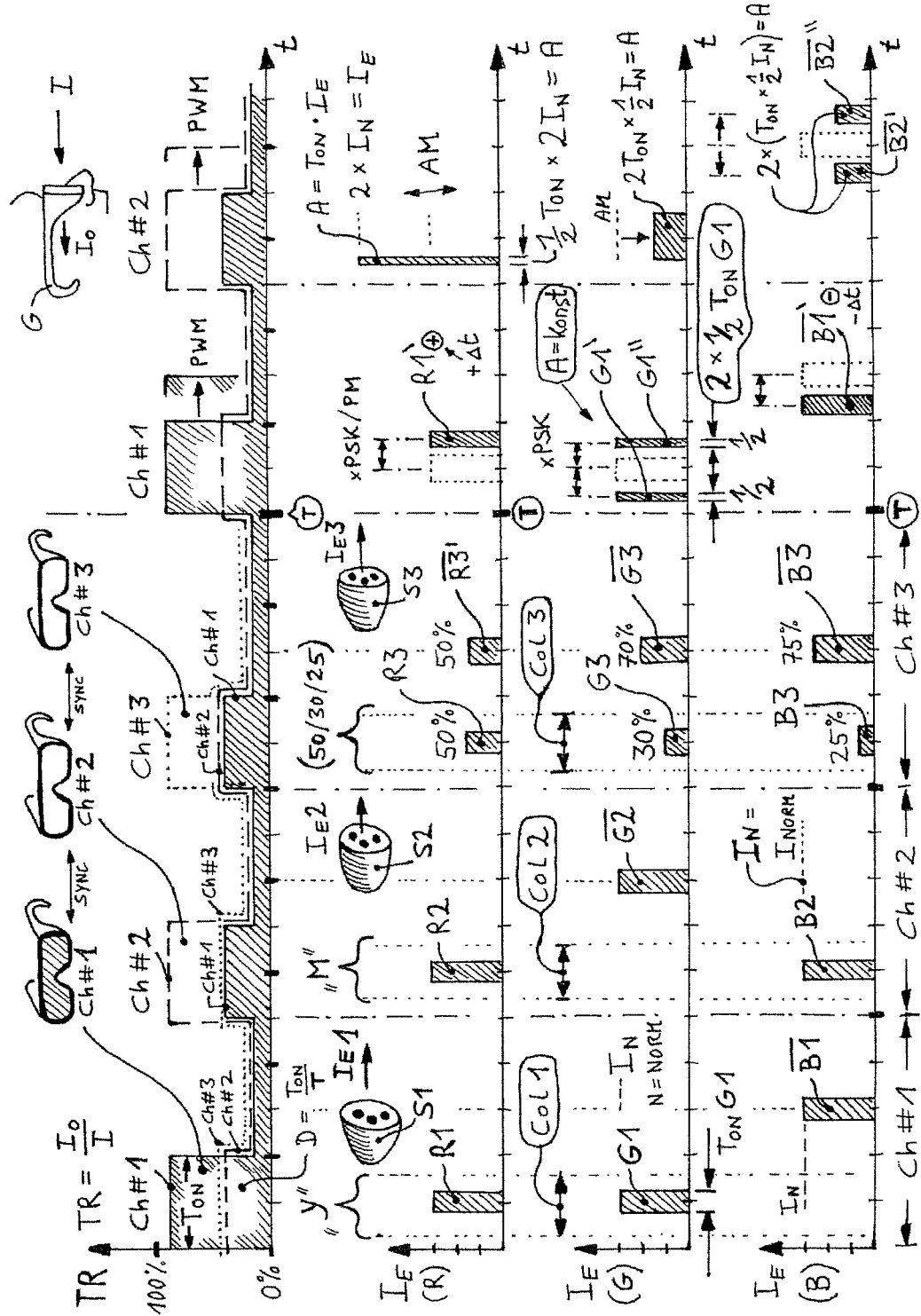
FIG. 6 shows a diagram of the transmission for an anti-glare system with RGB color coding.
Figure 7:
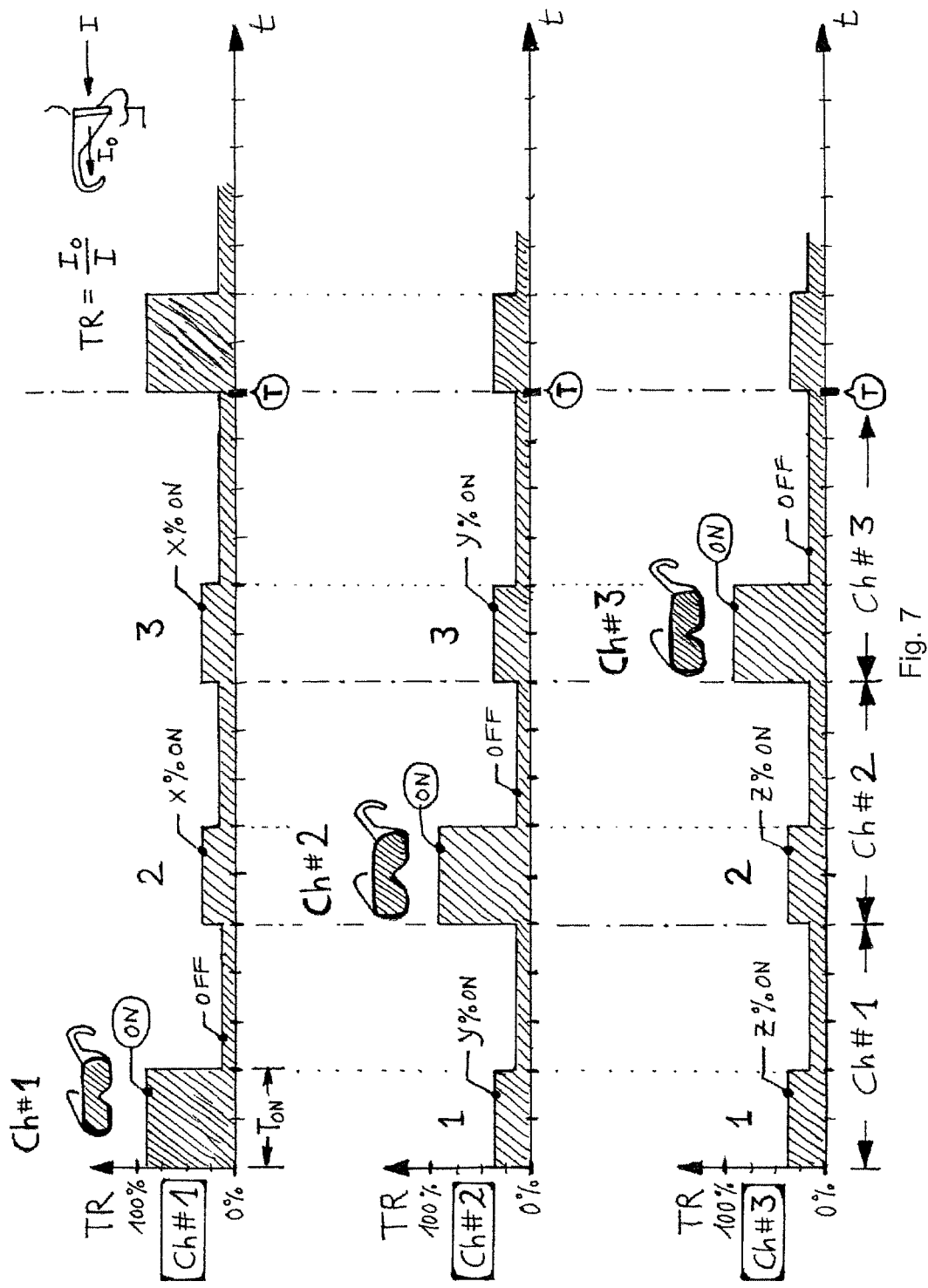
FIG. 7 shows a diagram illustrating the behavior of the various transmission levels TR (Ch#1, 2, 3) in an anti-glare system with RGB color coding.

The colors R=red, G=green, B=blue of the first channel Ch#1, shown separately in the lower 3 diagrams of FIG. 6 (IE of R, G, B), are not necessarily transmitted at the same time, but blue, for example, may also be transmitted with a slight time delay after red and green, but so shortly thereafter (a few milliseconds) that the human brain perceives them not as flicker, but always together as white light.

The difference for the wearer of the spectacles with respect to the channel designation is, however, that the color in the time slot $T_{on}$ in which the spectacles are opened (i.e. TR near 100%), the two colors red and green are transmitted from the own light source, while blue is only transmitted when the glasses are closed again (TR near 0%=OFF). In FIG. 6, this blue pulse is denoted by "B1 and top line", wherein the line above the letter signifies "negated". In this context, B1 is negated "blue, invisible to channel 1". In FIG. 6, this is symbolically indicated with Y above the curly bracket, since the sum of red and green results in the mixed color yellow. The wearer of the spectacles Ch#1 thus sees yellow light. Thus at least one multi-channel time-division multiplexing method is used with respect to the three color channels RGB and the respective spectacles.

In FIG. 6, it may be seen in channel 2 that the colors red and blue R+B mix in the time slot in which the spectacles are open, indicated by the curly bracket with M (for magenta since this color results from the mixture of red and blue). The wearer of the spectacles Ch#2 thus sees magenta-colored light.

In order for the wearer to have an idea of which channel his neighbor is lighting the target (e.g. for secret marking), the spectacles Ch#1 will only be slightly opened in the time slot of the channel, e.g. from close to 0% (spectacles closed) to 25% transmission (for example and freely adjustable), so that the wearer also sees the color magenta of the wearer of the spectacles Ch#2. However, since only 25% are visible, the wearer of the spectacles Ch#1 may concentrate more on his own light. Depending on the specific application, the degree of this attenuation may be freely changed between 0% (hidden from other team members) and 100% (to all others exactly as bright as their own color light source).

In fact, the "equal-time signal flanks" (solid, dashed and dotted lines in FIG. 6) overlap. For the sake of clarity, however, these are not shown as overlapping in FIG. 6, but minimally offset. The correct situation without this offset is illustrated in FIG. 7. It may be seen here that the spectacles or channel Ch#1 to Ch#3 are actually approximately equal in width (the same $T_{on}$), and that in the time slot of the other channels, the respective spectacles open very easily (e.g. about 25%). FIG. 7 thus represents the same situation as in FIG. 6, but with separate channels. The variables x %, y %, z % are intended here to show that each user may freely adjust the degree of recognisability of the other participants or colors according to their role in the team or according to personal preference.

FIG. 6 shows various exemplary modulation methods for the RGB light sources after expiration of the cycle time T. In analogy to the method of the constant energy per pulse (constant pulse area A) described at the outset, an RGB light source may also be modulated so that the individual color channels become narrower over time, while becoming higher in intensity and/or vice versa. This is easily possible because RGB LED or RGB LASER may be modulated in phase and amplitude relatively quickly, in particular at a significantly higher frequency than the spectacles. Thus, the exact phase (temporal position) of a single RGB pulse may be easily varied within the opening time $T_{on}$ of the spectacles, whether from total-cycle to total-cycle (approx. 70-140 Hz), or even extremely fast (>>1 kHz) within one cycle. By such an extremely fast phase variation, a phase modulation or a PSK may be applied to each individual RGB channel recognized by other spectacles or other receivers, e.g. it may also be used for "optical synchronization" of the spectacles, wherein the external and internal sensors OS, IS of the spectacles are always fast enough for this. This makes it possible to synchronize the spectacles within a team without radio contact (e.g. if this is undesirable or fails).

Apart from the color marking of objects, this phase modulation may also be encoded with a secret key and secret information contents in such a way that other information (e.g. what type of object, name, etc.) in the sense of a complete marking ("full information designation"), may be applied to a target or object. This complete information may, in turn, be decoded by the external and internal sensors OS, IS or also by separate receiving and decoding units.

In FIG. 6, the splitting of the third time beam from above (IE green) right, into two temporally half-wide pulses G1' and G1" (i.e. 2*54 $T_{on}$) is shown to the right above and designated A=constant, which corresponds to the already explained principle of the constant energy per pulse. In addition, "xPSK" is present which means that almost any phase modulation methods are possible with two separate pulses, similar to "di-bits", which may vary and jump in phase relation to each other or in relation to the time axis—theoretically also QPSK and similar procedures.

The splitting of the blue pulse in B2' and B2" (negated in each case at the top) is visible on the lower time beam (IE blue), but only at half height, i.e. amplitude 0.5 I standard. In this example, too, it becomes clear that the area A (i.e. the energy of the pulse array) remains constant. The amplitude information may also be used for the transmission of information, as in the case of an amplitude modulation AM, if appropriate also encoded with a secret key. It is also possible to use mixing of any FSK, x-PSK and AM methods.

The synchronization of the spectacles and own light sources is usually effected via radio signals, but may also take place optically. Synchronization may take place according to a certain hierarchy system, where one participant is always "master" and all others are always "slaves" (if the master fails, another specified "slave" becomes "master", etc.). This hierarchy may be determined, for example in the context of a common initialization routine (i.e. before a deployment), but also in the middle of the process (e.g. by radio or optically, due to a programmed encoded recognition, similar to multi-user IT systems such as LAN, WLAN, Token-Ring, etc.).

In addition, this overall multi-user system may be operated at the expense of a slightly smaller number of channels so that the pulse width modulation stroke of the spectacles is somewhat extended (see FIG. 6 at the top right of the diagram TR, to the right of the period T, identified by dashed flank and PWM. This extension of the PWM modulation stroke has the advantage that the spectacles may still be controlled with analogous gray light in slight darkening (e.g. 0 Lux to 100 Lux). Even in a multichannel group application with invisible color marking, the spectacles may operate seamlessly in the direction of daytime driving spectacles for analogous gray level control operation (as described above).

One's own light source does not necessarily have to consist exclusively of high-performance RGB LED or RGB LASER, but may also consist of high-power white-light LED which, for example, make up the main proportion of one's own light, while the red-green-blue components are only added for the purpose of coloring. This may be achieved by placing at least one or more RGB LED/LASER in the headlight/reflector next to the white light LEDs.

In the short time slot $T_{on}$ in which one's own spectacles are open, a specific color is also emitted from the source of one's own light, in addition to the white light pulse of the same area already shown in FIG. 2 (middle line); The two modulation methods (white light and invisible color marking) may be combined so that it remains a seamlessly functioning overall system. A glare weapon (described further above) may still be used in parallel to the invisible color marking described here, since this is only switched on when the spectacles of all the channels (Ch#1, 2, 3, etc.) are respectively closed (minimum transmission).

Optionally, as already described above, one's own light source may still be provided with a secret pulse hopping process, so that, for example, enemy units can not decode the colors and can not interfere with the entire system (spotlights with spectacles). Such an overall system may, of course, also be combined with the improved readability of displays (FIGS. 3 to 5).

Enhancing the Spatial Impression

Figure 8:
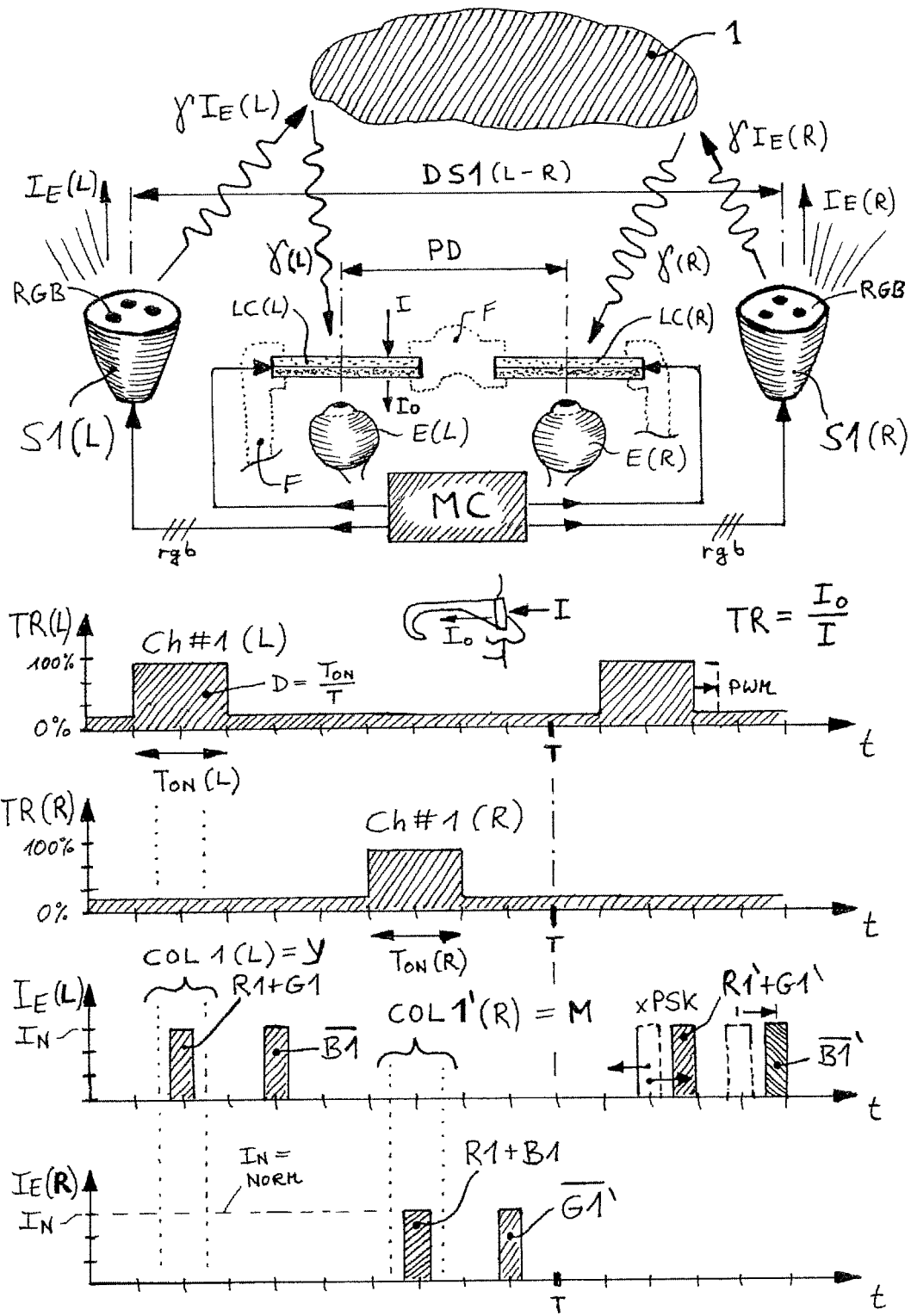
FIG. 8 shows a schematic representation of a system for enhancing the spatial impression.

Due to the limited human eye distance, objects at larger distances appear increasingly one-dimensional, which limits their recognisability. An embodiment of the overall system according to the invention, which can provide a remedy here, is shown in FIG. 8. The eye distance or the pupil distance PD may be seen there, as well as an arbitrary object 1, which is, e.g. (depending on the range of one's own two separated light sources S1(L) and S1(R), a few hundred meters away (even if, due to the limited drawing size, it appears immediately in front of the spectacles F). As described above, the spectacles F may regulate the brightness completely separately from one another (i.e. two separate channels/controls) in real time, taking into account intentional brightness differences (HDR vision) and/or physiological characteristics. It is, however, provided that the microcontroller MC may also control two separate own light sources. These are arranged on the right and left of the wearer of such a system, but at a greater distance DS1 (L–R) than the pupil distance PD of the wearer.

The mode of operation essentially corresponds to the RGB coding described above. The liquid crystals of the spectacles are then opened in succession, but never simultaneously, as shown in the diagram TR(L) and TR (R). Since this is still a time-division multiplexing process, this is at the expense of the free channels (users) so that the system may only process half as many users in a group application if all participants wanted to use the 3D enhancement. In contrast to the above-described RGB coding, however, a clearly distinguishable color is used per eye, e.g. yellow Y on the left and magenta M on the right.

For reasons of space, not every individual RGB channel is recorded in FIG. 8, but the color of the eye per eye channel L, R, is recognizable e.g. with the designation R1+G1 in the left channel IE(L). The light pulse B1 (negated) follows in the dead time slot (both lenses are closed) so that the external system appears in neutral white light to external third parties. In the right eye channel IE(R), for example, R1+B1 is added to M (magenta) in the dead time slot (both lenses are closed), followed by a green pulse G1 (negated). The basic principle is therefore essentially identical to the RGB coding, the description of which is further referred to above for further understanding. In FIG. 8, phase-modulation methods and xPSK methods already described on the right, beyond the period duration T, are also indicated.

Overall, this method leads to a better 3D perception, which is often referred to as "2.5D" in the specialist literature, since one can not look completely behind the object.

The method also works with a mixture of modulated white light and RGB light, so the system for mixing high frequency RGB LED/LASER modules with the above is compatible with somewhat slower white light LEDs.

The use of pure white light (i.e. without RGB sources) is also possible, in particular by increasing the distance between the sources DS1 (LR) and/or by flashing perceptibly on either side of the left and right channels e.g. with 2 to 10 Hz), which is possible by appropriate control of the self-illuminators and the spectacles.

LIDAR

Figure 9:
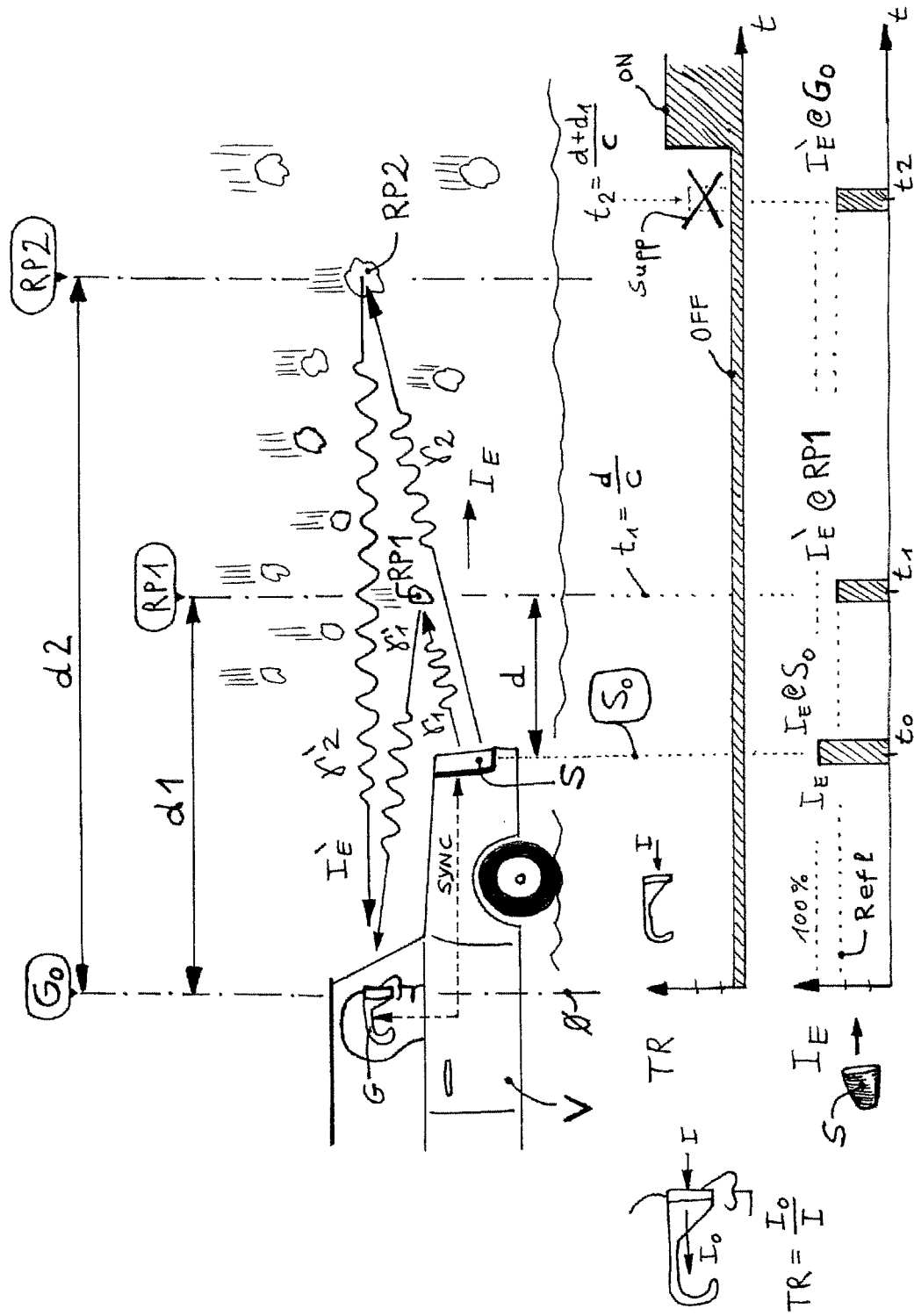
FIG. 9 shows a schematic representation of a system for improving the visual range by suppressing reflections in the close-up region through particle precipitation according to the LIDAR principle.

The system described so far may be so extended that light reflections of falling or ascending particles are hidden in the vicinity of the user. The problem occurs, for example, when driving at night in snowmobiles, where the snowflakes appear directly in front of the headlights because of the higher luminance, and obscure the view to a greater distance into the depth of the space. This situation is shown in FIG. 9: At a distance d1, a reflection particle RP1 reflects the light gamma 1 towards the driver.

If ultrasound pulses with pulse widths of a few nanoseconds are generated using special LASER or LED-based headlights, they may be controlled according to the LIDAR/LaDAR principle (known from the prior art) over their lifetime by means of an equally fast shutter, in order to be hidden/exposed to the users. For this purpose, the shutter lenses are so controlled that they only open at the (later) time t2 after the reflection of one's own headlight light on the spatially close particle RP1 has elapsed. The time axis in FIG. 9 is also to be understood as a spatial axis, since the distances (d=ct) and vice versa, result after multiplication by the constant light velocity c, and the corresponding times t are obtained by multiplying the sum of the light rays to give the distance traveled divided by the constant light velocity c (t2=(d+d1)/c). After the light has traveled through the distance d (headlights to near particles) and d1 (near particles to spectacles), the time t2 has elapsed. However, if the shutter of the glasses opens only after the time t2 has elapsed, as represented by TR (=on) in FIG. 9, the light reflex is suppressed (supp. in FIG. 9) and is therefore not visible.

Snowflakes or other particles (or mist) are not really invisible—they appear rather as black dots—but the overall view into the depth of the space is significantly improved due to reduced glare.

Own Light Recognition or Suppression

Figure 10:
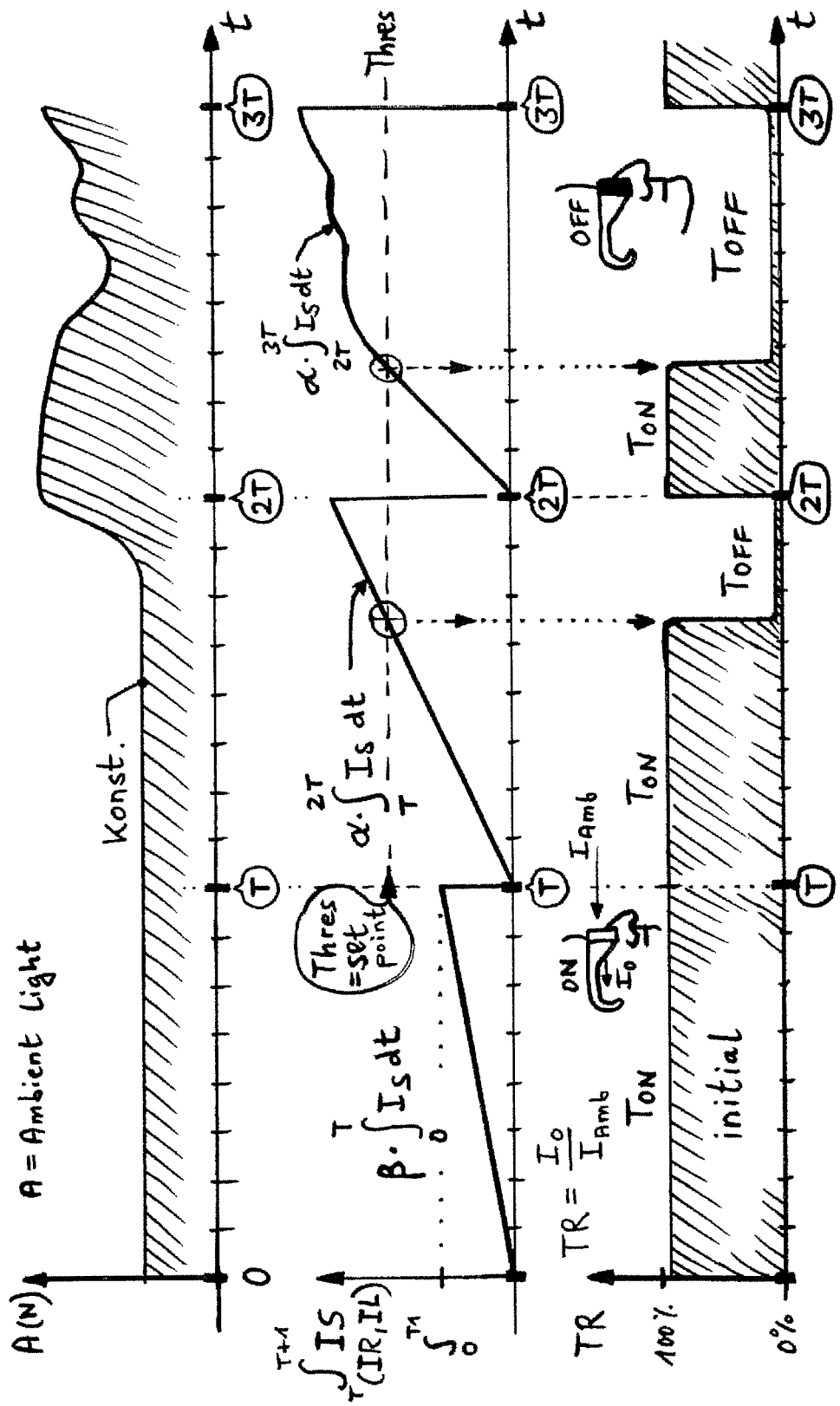
FIG. 10 shows a diagram for the own light suppression of a glare suppression system.

In the following, reference is made to FIGS. 10 and 11. A means ambient light, U means extraneous light (unwanted, for example sunlight), and W means own light (wanted). The distinction between U and W is as follows:

Since the microcontroller knows the points in time when it turns on its own headlight W, it can query the outer photosensor, which is more than sufficiently fast, in a time slot shortly before (or shortly after) the light pulse is transmitted—shown in FIG. 10 by N−1 or N+1, where N is the $N^{th}$ time slot of the transmitted light pulse. The following applies:

$$A(t)=U(t)+W(t) \quad (1),$$

or discretely queried, where N=average value from a time slot N according to FIG. 10:

$$A(N)=U(N)+W(N) \quad (2),$$

It is assumed that the interfering light does not change significantly in time "shortly before or shortly after" the light pulse since the period between N−1 and N and N+1 is very small.

$$U(N)=U(N-1)=U(N+1) \quad (3).$$

Other, e.g. more complex, experience-based averaging methods, or the simple arithmetic mean may be selected. In any case, it is assumed that with this method, the interfering light value U (N) may be determined in the time slot N with very high accuracy, provided that the ambient light does not change very quickly and is not pulsed on its own. If one assumes that the additional light from one's own beam is added to the ambient light according to formula (1), then it is always greater than the ambient light in the neighboring time slots for A (N):

$$A(N)>A(N-1) \text{ and } A(N)>A(N+1) \quad (4).$$

Further, the normal return reflection of one's own light from remote and not very reflective objects, i.e. from a normal scenery/environment (road, forest, field, in the house with large rooms), is rather small compared to a massive interfering light like strong sunlight, so that in the extreme application of massive glare suppression, the following applies:

$$W(N)<<U(N) \quad (6).$$

Often one speaks of a "delta", which is added or omitted, for very small quantities, so that the formula (1) may also be written as:

$$A(N)=W(N)=A(N)-U(N) \quad (7).$$

Since, in a 70 Hz system, a A (N) is measured 70 times per second, these values may in turn be averaged, e.g. over a meaningful small period of time that is fast enough to adequately protect the eye with respect to potential emergency shutdown or down-regulation of one's own headlights when inadvertently looking into these headlights, e.g. over a period of one-third or one-eighth of a second (x=e.g. 125 ms to 300 ms):

Mean value: MA (N)=MW (N)=e.g. flowing arithmetic mean of all W (N) in period T=t to t+x This value may then be fed to a threshold value switch-off, or may be used for a more uniform (analog) down-regulation of one's own headlights.

EXAMPLE

S=Decision threshold for the emergency stop of one's own headlights

W (N)<S one's own headlights continues normally

W (N)>=S one's own headlights is switched off

As a rule-of-thumb formula, it may be said that an empirically determined multiple M(multiplier) brighter appearing light serves as a threshold:

$$S=M*U(N) \quad (8.1)$$

Or, if one does not want to refer to U (N), i.e. make independent of so-called "scenarios", such as excessive or no glare—then one simply formulates self-referentially through multiples of W(N), e.g.:

S=50% to 500% of the usual experience value of W (N) (8.2).

In FIG. 10, it is assumed that the spectacles are in the "night mode" at the control stop, so that all Ton times are equally narrow (e.g. 5% from the cycle time T). As a fully-filled black beam, the desired light W (N) is shown in the graph in the center of the image. Since a back-reflection from an object is only very weak in normal cases, the black beam is very small for the first two cycles. Irrespective of how much other interfering light U is added, exemplarily shown in the cycle T, the headlight light shown below remains at a constant intensity IE1, i.e. the headlight has already reached its intensity maxima with 16×IN, for example, which can not be increased further. If, however, the ratio of wanted to unwanted changes significantly, as shown in 2T (1:1), then the headlight intensity is reduced R. In the extreme case 3T, it may be switched off (IE near zero).

Measurement with the IS Inner Sensor—in Combination with Short, One-Off Flashes

In addition, the delta, i.e. W(N), may be measured as an alternative to the above method or for test purposes in a cycle T, as described above, in order then, exceptionally and exclusively only in the following cycle 2T, the lamp S instead of the expected light pulse, thus deliberately exposing a light pulse as dropping out. Because such an individual "dropout" in cycle 2T is only one of a total of 70 light pulses per second (in the case of a 70 Hz system), wherein this is not noticed by the user or by external third parties.

If DC light is present, or if the glasses run synchronously with an AC interfering light, then one may even assume that the interfering light does not change very much in the very short time interval N−1, N, N+1 and remains largely constant from one cycle T until the next cycle 2T:

$$U(N,T)=U(N,2T) \quad (9)$$

The internal sensor IS may then measure the delta W(N) in the cycle T, whereas in the cycle 2T this delta W(N) no longer appears because of the one's own switched-off headlight. Thus, it may occur in the same time slot N, that an additional measurement of W(N) may be carried out by means of the internal sensor, without having to rely on the above-explained measurement with the outside sensor (in the time slots N−1, N, N+1). If one uses both methods (i.e. the internal sensor with the light source and the light sensor once switched off) simultaneously, then the accuracy and reliability of the W(N) measurement may be increased with this redundancy. Conflicting or illogical measurements may be determined and correspondingly corrected by simultaneous application of both methods via the microcontroller.

No DC backlight source, but accidental view into own source of light It may be assumed in an extreme case that in the case of a very dark night and a disturbance-free view (e.g. completely alone in the forest), the following applies $$U(N)=0$$

It follows from the above formula (2)=A (N)=U (N)+W (N) that the following applies $$A(N)=W(N)$$

In this case, the spectacles may also be completely open/transparent, while the headlamp may also be switched on permanently or apparently or largely permanently (e.g. separated measuring pulses every 300 ms), so that the delta measurements described above may also take place. The spectacles are automatically transferred back into the usual PWM modulation mode only when sudden disturbances occur.

Strong AC back-light source, e.g. electrical artificial light source, e.g. from the 50/60 Hz low-voltage network The external sensor OS or OL, OR has three main characteristics:

1) It is comparatively much faster than industrial artificial light (100-120 Hz) and may trigger this electronically and may easily be detected by means of microcontrollers.

2) It is also standardized as a measuring device (it can output values in lux or comparable light technical units or in corresponding voltage equivalents) and is weighted with the human eye sensitivity curve so that it can also measure light intensity.

3) It is preferably, but not necessarily, identical to the internal sensor IS so that the microcontroller may be instantaneously measured in real-time "compensating measurements" between the inside (through the LCD) and the outside (bypassing the LCD).

If there is only one single dominant artificial light source, so that a cyclic 100/120 Hz oscillation can be detected by the external sensor, it determines the start time $T_{NUII}$ of the fundamental frequency of the PWM of the spectacles and the frequency of the PWM, wherein the brightness maximum of the external light source is always exactly at the beginning of a cycle and may be measured immediately by the external sensor OS and also by the internal sensor IS. The internal sensor IS may also measure this maximum brightness of the artificial light source because at the beginning of a cycle, the spectacles are always "open", i.e. the liquid crystal cell is transparent. Thus, the external sensor OS and the internal sensor IS basically measure the same light, but with the slight difference that the transparent LCD is located in front of the internal sensor IS, so that IS receives a little less light—i.e. minus the temperature-dependent and aging-dependent transmission in the continuous state—e.g. 50% less with crossed polarizers (polarizer-analyzer position).

Furthermore, the internal and external sensors IS1 and OS1 are also arranged spatially very closely on an imaginary axis, e.g. not more than 3 mm apart—also called the "measuring pairs No. 1" (MP1). Thus, even spatial frequencies OF (in the broadest sense "stripe pattern") of OF>3 mm may in no way lead to measurement errors. In addition, a further measuring pair MP2 consisting of IS2 and OS2 exists in each case orthogonally to the aforementioned measuring pair MP1, so that checkerboard patterns, i.e. spatial frequencies, which run perpendicular to the aforementioned spatial frequencies, may be correspondingly detected if these are more than 3 mm. Both measuring pairs (MP1 and MP2) provide values which may be evaluated by the microcontroller in such a way that "geometric mean values" may be formed according to the imaginary triangle between the pupil centerpoint position and the sensor arrangement.

Integration within One Cycle

Figure 11:
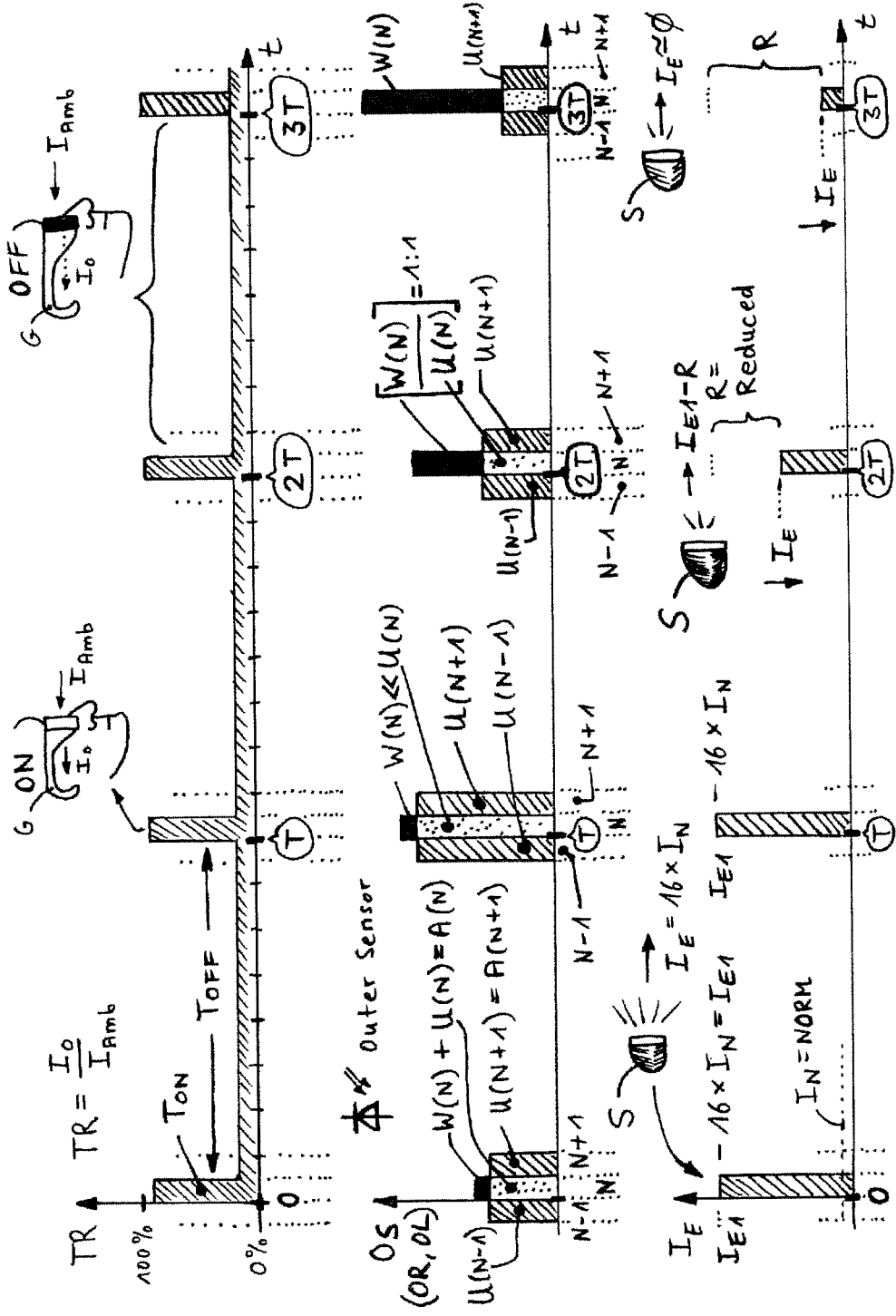
FIG. 11 shows a further diagram for own light suppression, which shows the initialization phase.

The internal sensor IS measures the light incident through the LC and integrates this light during an idle initialization phase in the very first cycle of 100 or 120 Hz in which the spectacles remain completely open (see FIG. 11). Since it is only a single cycle of a synchronous 100 or 120 Hz system (i.e. from further subsequent 109 or 119 controlled cycles), the human eye does not perceive this. However, a first integration result of the cycle T is present.

If the sensor IS forms an integral via, for example, a constant (DC interfering light), then a straight ascending line (see FIG. 11) results which, after exceeding a setpoint value threshold (setpoint trigger), causes the complete closing of the spectacles (hard on-off keying via PWM).

This also has the advantage that a decision and reaction is still carried out within a respective cycle T without the T+1 or T−1 or other further cycles having to be included, as would normally be necessary in the case of an "analogous mathematical calculation in the frequency domain of an APID controller". Therefore, no Fourier transformation is necessary—neither FFT nor FT, DFT, etc.

The so-called control is thus "hard" in this case and reacts in real time already in cycle T to a setpoint value—also called "microscopic control".

The So-Called "Macroscopic Control".

However, this microscopic integration value from the $N^{th}$ cycle may be stored in a volatile intermediate memory so that it may be used as a "floating/sliding mean value correction value", i.e. for further successive integration values. As a macroscopic integration value—approximately within a quarter or third of a 100 Hz or 120 Hz cycle (i.e. within imperceptible fractions of a second).

Thus the regulation always reacts correctly in the case of fluctuating artificial light. FIG. 11 shows the initialization phase with a still unknown output or unknown outer brightness (weighting factor beta), then in cycle 2, followed by a cycle (weighting factor alpha) normalized to 1 or maximal brightness and modulation stroke featuring the integral ($T_0$ff) when the target value Thres is reached.

In the third cycle, for example, it is shown how the outer brightness has increased and also fluctuates. The corresponding integral (graph in the center of the image) now runs steeper so that the setpoint value Thres is reached more quickly and consequently the spectacles close earlier in time—$T_{OFF}$ is thus longer than in the cycle before. The integral values are set to zero at the end of each cycle so that each cycle is controlled in real-time in its transmittance TR.

Scenario: Several strong AC back-light sources, e.g. electrical artificial light sources, e.g. from various networks, so that frequency mixtures are present.

A mixture of various superimposing frequencies may cause the external sensor to no longer be able to synchronize with a certain interference frequency. However, this may also have advantages, since a mixture in the oscillogram is represented as "noise", which hardly has more valleys and misfires of extraneous light than results from a stable "ground noise" due to the superimpositions. In this case, the spectacles or microcontrollers will abort the attempt to synchronize and simply switch to a typical preset operating frequency, e.g. to 70 Hz, in order to work there unintentionally according to the above integration scheme.

Scenario: Several strong pulsed back-light sources, e.g. electrical LED type light sources, e.g. such as the present or similar systems Due to the immediate integration within a cycle, the spectacles may close as soon as a threshold is reached. Since the dynamic range and the measuring speed of the external and internal sensors are always faster and better than the human eye, extreme intensities and harmful performances may also be avoided, such as, for example, extremely short light pulses of high energy, such as, e.g. from pulsed Q-switch lasers or pulsed LEDs.

The human eye can no longer perceive and react from a certain growing intensity with pulses which are becoming shorter and shorter at the same time, as the cornea and retina are in danger of being harmed.

Reaction of the Spectacles in Case of Doubt:

The spectacles therefore tend to "close" (eye protection) at high intensities—while they tend to be "open" in the case of low intensities, but in the case of chaotic unspecifiable frequency patterns, which may not be synchronized, a kind of "average brightness" is determined by integrating and averaging over several cycles T (e.g. over 300 ms), as if it were noise or a nearly uniform source—whereas, however, it is basically in the PWM night vision and dark range (5% to approx. 20% open PWM time slot with appropriately pulsed spotlight).

According to an embodiment of the invention, a system for visual enhancement by glare suppression comprises:
spectacles for a wearer with at least one eye, comprising at least one spectacle lens;
wherein the at least one spectacle lens has a liquid crystal cell (LC), the transmission of which may be varied by a suitable control;
wherein the liquid crystal cell (LC) is so designed that the transmission (TR) of the liquid crystal cell (LC) may be switched between high and low transmission states; and with
means for controlling or regulating the times of the state of high transmission (Ton) of the liquid crystal cell (LC);
at least one sensor (IL, IR) for measuring the brightness of the visible light incident thereon;
wherein the at least one sensor (IL, IR) is arranged on the eye-side of the spectacle lens;
wherein the at least one sensor (IL, IR) measures the brightness through the at least one spectacle lens; and with
a closed-loop control circuit (MC) for regulating the transmission of the liquid crystal cell (LC);
wherein the regulation is so designed that the times of the state of high transmission (Ton) become shorter with increasing glare;
wherein a setpoint value for the brightness at the eye of the spectacle wearer is preset;
wherein the control circuit uses the brightness measured by the sensor as the actual value; and with
a display with
means for controlling the lighting times and the luminous intensity of the display in order to illuminate during the times of the state of high transmission (Ton) of the liquid crystal cell (LC);
wherein the temporal integral of the product of
the luminous intensity of the display and
the transmission (TR) of the liquid crystal cell (LC) remains constant within a predetermined tolerance upon a change in the times of the state of high transmission (Ton).

According to an embodiment, the system is characterized in that
the display comprises
a display on the side of the spectacle lens facing away from the eye, and/or
a display on the eye-side of the spectacle lens, and/or
a head-up display (HUD).

According to an embodiment, the system is characterized in that
the liquid crystal cell (LC) is so designed that it can change its transmission from 90% to 10% and from 10% to 90% in a maximum of 10 ms.

According to an embodiment, the system is characterized in that
25.1 the spectacles have a spectacle frame, wherein
25.2 the spectacle frame seals the at least one eye of the spectacle wearer against the ambient light in a light-tight manner.

According to an embodiment, the system is characterized in that
the setpoint value of the control circuit prescribes a brightness at the eye of 20 to 400 lx.

According to an embodiment, the system is characterized in that
the brightness of the ambient light is derived from the setpoint value and a control signal of the control circuit.

According to an embodiment, the system is characterized in that at least one further brightness sensor (OL, OR) is arranged on the side of the spectacles facing away from the eye (external sensor) and determines the brightness of the ambient light.

According to an embodiment, the system is characterized in that the setpoint value of the control circuit may be changed as a function of the brightness of the ambient light; and the change in the setpoint value is slower than the control of the transmission of the liquid crystal cell by a factor of at least 10.

According to an embodiment, the system is characterized in that the setpoint value is changed in preset stages;

wherein the stepwise change of the setpoint value is slower than the control of the transmission of the liquid crystal cell by a factor of at least 100.

According to an embodiment, the system is characterized in that the regulation is so designed that it reacts to extreme brightness values within 10 ps to one second such that the liquid crystal cell (LC) is set to the state of low transmission.

According to an embodiment, the system is characterized in that the glasses comprise two spectacle lenses for two eyes of a spectacle wearer;

respectively an eye-side sensor for each spectacle lens for measuring the brightness of the visible light incident on the respective eye; and a control circuit for each spectacle lens.

According to an embodiment, the system is characterized in that the setpoint values for the two eyes differ from one another by 1% to 60%.

According to an embodiment, the system is characterized in that when regulating the brightness of the visible light incident on an eye the regulation of the brightness for the other eye is taken into account.

According to an embodiment, the system is characterized in that an eye tracker (ET) capable of determining the viewing direction of the eye is provided;

wherein the at least one sensor (IL, IR) comprises an imaging system with a camera or at least three sensors which span a coordinate system or a compound eye;

wherein the at least one sensor (IL, IR) can determine the brightness of the visible light which is incident upon it from the viewing direction of the eye determined by the eye tracker (ET); and wherein the control circuit (MC) takes the brightness measured by the sensor in the viewing direction of the eye as the actual value.

According to an embodiment, the system is characterized in that the control circuit is so designed that, when determining the brightness from the viewing direction of the eye, it can take into account a user-specific eye/retina sensitivity curve for weighting the brightness.

According to an embodiment, the system is characterized in that the measured values of the sensors and/or the setpoint values of the control circuits and/or the brightness of the environment derived therefrom, are connected to a geo-coordinate signal of a geo-coordinate receiver and recorded.

According to an embodiment, the system is characterized in that the at least one spectacle lens has a further liquid crystal cell, the transmission of which may be varied by a suitable control, wherein the further liquid crystal cell is arranged behind or in front of the liquid crystal cell (LC) in the viewing direction.

According to an embodiment, a method for visual enhancement by glare suppression is presented herein. The method comprises spectacles for a wearer with at least one eye are provided, wherein the spectacles are so designed that they comprise the following:

at least one spectacle lens;

wherein the at least one spectacle lens has a liquid crystal cell (LC), the transmission of which may be varied by a suitable control;

wherein the liquid crystal cell (LC) is so designed that the transmission (TR) of the liquid crystal cell (LC) may be switched between high and low transmission states;

means for regulating or controlling the times of the state of high transmission (Ton) of the liquid crystal cell (LC);

at least one sensor (IL, IR) for measuring the brightness of the visible light incident thereon;

wherein the at least one sensor (IL, IR) is arranged on the eye-side of the spectacle lens;

wherein the at least one sensor (IL, IR) measures the brightness through the at least one spectacle lens;

a closed-loop control circuit (MC) to control the transmission of the liquid crystal cell (LC);

wherein the regulation is so designed that the times of the state of high transmission (Ton) become shorter with increasing glare;

wherein a setpoint value is preset for the brightness at the eye of the spectacle wearer;

wherein the control circuit takes the brightness measured by the sensor as the actual value;

a display is provided, wherein the display is so formed that it comprises the following:

means for controlling the lighting times and the luminous intensity of the display such a way that it illuminates during the times of the state of high transmission (Ton) of the liquid crystal cell (LC);

wherein the temporal integral of the product of the luminous intensity of the display and the transmission (TR) of the liquid crystal cell (LC) remains constant within a predetermined tolerance upon a change in the times of the state of high transmission (Ton).

According to an embodiment of said invention, a system for visibility enhancement by glare suppression is presented herein, The system having:

spectacles for a wearer with at least one eye, with at least one spectacle lens;

wherein the at least one spectacle lens has a liquid crystal cell (LC), the transmission (TR) of which may be varied by a suitable control;

wherein the liquid crystal cell (LC) is so designed that the transmission (TR) of the liquid crystal cell (LC) may be switched between high and low transmission states; and with means for controlling or regulating the times of the state of high transmission (Ton) of the liquid crystal cell (LC);

and with a light source (S) comprising means for controlling the lighting times and the luminous intensity of the light source (S) such that it illuminates during the times of the state of high transmission (Ton) of the liquid crystal cell (LC);

wherein the temporal integral of the product of
the luminous intensity of the light source (S) and
the transmission (TR) of the liquid crystal cell (LC)
remains constant within a predetermined tolerance upon a change in the times of the state of high transmission (Ton);
wherein the regulation or control of the liquid crystal cell (LC) and of the light source (S) is so formed
that the temporal position of the times of the high transmission state (Ton) within a period of times of the high transmission state (Ton) and times of the low transmission state (Toff) may be altered continuously or discontinuously; and/or
that the duration of a period of times of the high transmission state (Ton) and times of the low transmission state (Toff) may be altered continuously or discontinuously; wherein the changes are determined by a secret coding key.

System according to the preceding claim,
characterized in that
the spectacles further comprise at least one sensor (IL, IR) for measuring the brightness of the visible light incident on the sensor;
wherein the at least one sensor (IL, IR) is arranged on the eye-side of the spectacle lens;
wherein the at least one sensor (IL, IR) measures the brightness through the at least one spectacle lens;
the spectacles further comprise a closed-loop control circuit (MC) for regulating the transmission of the liquid crystal cell (LC);
wherein a setpoint value is preset for the brightness at the eye of the spectacle wearer;
wherein the control circuit takes the brightness measured by the sensor as the actual value.

According to an embodiment, the system is characterized in that
the at least one sensor (IL, IR) comprises
an imaging system with a camera or
at least three sensors which span a coordinate system, or
a compound eye;
the spectacles further comprise an eye tracker (ET) capable of determining the viewing direction of the eye;
the at least one sensor can determine the brightness of the visible light which is incident
upon it from the viewing direction of the eye determined by the eye tracker (ET); and
the control circuit takes the brightness measured by the sensor in the viewing direction of the eye as the actual value.

According to an embodiment, the system is characterized in that
a second light source for the dazzling of a living being, an optical sensor or a camera, which illuminates during the times of the low transmission (Toff) state of the liquid crystal cell (LC).

According to an embodiment, the system is characterized in that
the light source is a light source for the dazzling of a living being, an optical sensor or a camera.

According to an embodiment, the system is characterized in that
the light source is a display.

According to an embodiment, a method for visual enhancement by glare suppression, comprising the following steps is presented herein:
spectacles for a wearer with at least one eye are provided, wherein the spectacles have at least one spectacle lens;
wherein the at least one spectacle lens has a liquid crystal cell (LC), the transmission (TR) of which may be varied by a suitable control;

wherein the liquid crystal cell (LC) is so selected that the transmission (TR) of the liquid crystal cell (LC) may be switched between high and low transmission states;
wherein the times of the high transmission (Ton) states of the liquid crystal cell (LC) are controlled or regulated;
a light source (S) is provided;
wherein the luminance times and the intensity of the light source (S) are controlled or regulated such that the latter illuminates during the times of the state of high transmission (Ton) of the liquid crystal cell (LC), wherein
the temporal integral of the product of
the intensity of the light source (S) and
the transmission (TR) of the liquid crystal cell (LC)
remains constant within a predetermined tolerance upon a change in the times of the state of high transmission (Ton);
wherein the regulation or control of the liquid crystal cell (LC) and of the light source (S) is so formed
that the temporal position of the times of the state of high transmission (Ton) within a period of times of the high transmission state (Ton) and times of the low transmission state (Toff) may be changed continuously or discontinuously; and/or
that the duration of a period of times of the high transmission state (Ton) and times of the low transmission state (Toff) may be altered continuously or discontinuously;
wherein the changes are determined by a secret coding key.

According to an embodiment, a system for dazzling a living being, an optical sensor or a camera is presented herein. The system comprising,
spectacles for a wearer with at least one eye, with
at least one spectacle lens;
wherein the at least one spectacle lens has a liquid crystal cell (LC), the transmission of which may be varied by a suitable control;
wherein the liquid crystal cell (LC) is so designed that the transmission (TR) of the liquid crystal cell (LC) may be switched between high and low transmission states; and with
means for controlling the times of the state of high transmission (Ton) of the liquid crystal cell (LC);
a light source for dazzling a living being, an optical sensor or a camera,
which illuminates during the times of the low transmission state (Toff) of the liquid crystal cell (LC);
wherein the regulation or control of the liquid crystal cell (LC) and the light source for dazzling is so formed
that the temporal position of the times of the high transmission state (Ton) within a period of times of the high transmission state (Ton) and times of the low transmission state (Toff) may be altered continuously or discontinuously; and/or
that the duration of a period of times of the high transmission state (Ton) and times of the low transmission state (Toff) may be altered continuously or discontinuously;
wherein the changes are determined by a secret coding key.

According to an embodiment, the system is characterized in that
a second light source (S);
means for controlling or regulating the lighting times and the luminous intensity of the second light source (S) such that it illuminates during the times of the state of high transmission (Ton) of the liquid crystal cell (LC).

According to an embodiment, the system is characterized in that
the second light source is a display.

According to an embodiment, the system is characterized in that
the spectacles further comprise at least one sensor (IL, IR) for measuring the brightness of the visible light incident on the at least one sensor;
wherein the at least one sensor is arranged on the eye-side of the spectacle lens;
wherein the at least one sensor measures the brightness through the at least one spectacle lens;
the spectacles further comprise a closed-loop control circuit (MC) for regulating the transmission of the liquid crystal cell (LC);
wherein a setpoint value is preset for the brightness at the eye of the spectacle wearer;
wherein the control circuit takes the brightness measured by the sensor as the actual value.

According to an embodiment, the system is characterized in that
the sensor (IL, IR) comprises
an imaging system with a camera or
at least 3 sensors which span a coordinate system, or
a compound eye;
the spectacles further comprise an eye tracker (ET) capable of determining the viewing direction of the eye;
the sensor can determine the brightness of the visible light which is incident upon it from the viewing direction of the eye determined by the eye tracker (ET); and
the control circuit takes the brightness measured by the sensor in the viewing direction of the eye as the actual value.

According to an embodiment, the system is characterized in that
the liquid crystal cell (LC) is so designed that it can change its transmission from 90% to 10% and from 10% to 90% in a maximum of 10 ms.

According to an embodiment, the system is characterized in that
the spectacle frame seals the at least one eye of the spectacle wearer against the ambient light in a light-tight manner.

According to an embodiment, the system is characterized in that
the nominal value of the control circuit prescribes a brightness at the eye of 20 to 400 lx.

According to an embodiment, the system is characterized in that
the brightness of the ambient light is derived from the setpoint value and a control signal of the control circuit.

According to an embodiment, the system is characterized in that
at least one further brightness sensor (OL, OR) is arranged on the side of the spectacles facing away from the eye (external sensor) and determines the brightness of the ambient light.

According to an embodiment, the system is characterized in that
wherein the setpoint value of the control circuit may be varied as a function of the brightness of the ambient light; and
wherein the change in the setpoint value is slower by a factor of at least 10 than the control of the transmission of the liquid crystal cell.

According to an embodiment, the system is characterized in that
the setpoint value is changed in preset steps;
wherein the stepwise change of the setpoint value is slower than the control of the transmission of the liquid crystal cell by a factor of at least 100, and
has hysteresis in its course.

According to an embodiment, the system is characterized in that
the control is so designed that it reacts to extreme brightness values within 10 ps to one second such that the liquid crystal cell (LC) is set to the state of low transmission.

According to an embodiment, the system is characterized in that
two spectacle lenses for two eyes of a spectacle wearer;
two eye-side sensors for measuring the brightness of the visible light incident on the respective eye; and by
a control circuit for each eye.

According to an embodiment, the system is characterized in that
the setpoint values for the two eyes differ from one another by 1% to 60%.

According to an embodiment, the system is characterized in that when regulating the brightness of the visible light incident on an eye the regulation of the brightness for the other eye is taken into account.

According to an embodiment, the system is characterized in that
light sources arranged on the side of the spectacles facing away from the eye; wherein the light sources are controlled as a function of the viewing direction of the spectacle wearer.

According to an embodiment, the system is characterized in that
the measured values of the sensors and/or setpoint values of the control circuits and/or the brightness of the environment derived therefrom, are connected to a geo-coordinate signal of a geo-coordinate receiver and recorded.

According to an embodiment, the system is characterized in that
the at least one spectacle lens has a further liquid crystal cell, the transmission of which may be varied by a suitable control,
wherein the further liquid crystal cell is arranged behind or in front of the liquid crystal cell in the viewing direction.

According to an embodiment of an invention, a method for dazzling a living being, an optical sensor or a camera is provided herein. The method comprises:
spectacles for a wearer with at least one eye are provided;
wherein the spectacles have at least one spectacle lens;
wherein the at least one spectacle lens has a liquid crystal cell (LC), the transmission of which may be varied by a suitable control;
wherein the liquid crystal cell (LC) is so designed that the transmission (TR) of the liquid crystal cell (LC) may be switched between high and low transmission states;
wherein the spectacles further comprise means for controlling the higher transmission state (Ton) of the liquid crystal cell (LC);
a light source is provided for dazzling a living being, an optical sensor or a camera, which illuminates during the times of the low transmission state (Toff) of the liquid crystal cell (LC);
wherein the regulation or control of the liquid crystal cell (LC) and the light source for dazzling is so formed
that the temporal position of the times of the high transmission state (Ton) within a period of times of the high transmission state (Ton) and times of the low transmission state (Toff) may be altered continuously or discontinuously; and/or that the duration of a period of times of the high transmission state (Ton) and times of the low transmission state (Toff) may be altered continuously or discontinuously;

wherein the changes are determined by a secret coding key.

According to an embodiment of an invention, a system for visibility enhancement by glare suppression is provided herein; the system with:

spectacles for a wearer with at least one eye, with at least one spectacle lens;

wherein the at least one spectacle lens has a liquid crystal cell (LC), the transmission of which may be varied by a suitable control;

wherein the liquid crystal cell (LC) is so designed that the transmission (TR) of the liquid crystal cell (LC) may be switched between high and low transmission states; and with at least one sensor (IL, IR) for measuring the brightness of the visible light incident on the at least one sensor; and with a closed-loop control circuit (MC) for regulating the transmission of the liquid crystal cell (LC);

wherein a setpoint value is preset for the brightness at the eye of the spectacle wearer; wherein the control circuit takes the brightness measured by the at least one sensor (IL, IR) as the actual value;

wherein the regulation or control is so formed that the times of the state of high transmission (Ton) become shorter with increasing glare; and with a light source (S) with means for controlling or regulating the lighting times and the luminous intensity of the light source (S) such that it illuminates during the times of the state of high transmission (Ton) of the liquid crystal cell (LC);

wherein the temporal integral of the product of the luminous intensity of the light source and the transmission (TR) of the liquid crystal cell (LC) remains constant within a predetermined tolerance upon a change in the times of the state of high transmission (Ton);

wherein the at least one sensor (IL, IR) measures the brightness of the visible light incident thereon exclusively in the times of the low transmission state (Toff).

According to an embodiment, the system is characterized in that the sensor also measures the brightness of the visible light incident thereon in the times of the state of high transmission (Ton);

wherein these measurements are carried out separately from the measurements in the times of the low transmission state (Toff).

According to an embodiment, the system is characterized in that a control of the light source (S) such that, in the case in which the measured brightness during the times of the high transmission state (Ton) is higher than a predetermined threshold above the brightness during the times of the low transmission state (Toff), the light source (S) is switched off or its luminous intensity is reduced.

According to an embodiment, a method for visibility enhancement by glare suppression is provided herein. The method comprising the following:

spectacles for a wearer with at least one eye are provided;

wherein the spectacles are so designed that they have at least one spectacle lens;

wherein the at least one spectacle lens has a liquid crystal cell (LC), the transmission (TR) of which may be varied by a suitable control;

wherein the liquid crystal cell (LC) is so designed that the transmission (TR) of the liquid crystal cell (LC) may be switched between high and low transmission states;

providing at least one sensor (IL, IR) for measuring the brightness of the visible light incident on the sensor;

wherein the at least one sensor (IL, IR) is arranged on the eye-side of the spectacle lens;

wherein the at least one sensor (IL, IR) measures the brightness through the at least one spectacle lens;

the transmission of the liquid crystal cell (LC) is controlled;

wherein a setpoint value is preset for the brightness at the eye of the spectacle wearer;

wherein the control circuit takes the brightness measured by the at least one sensor (IL, IR) as the actual value;

wherein the control is so designed that the times of the state of high transmission (Ton) become shorter with increasing glare;

a light source (S) is also provided;

the lighting times and the luminous intensity of the light source (S) are so controlled that it illuminates during the times of the state of high transmission (Ton) of the liquid crystal cell (LC);

wherein the temporal integral of the product of the luminous intensity of the light source (S) and the transmission (TR) of the liquid crystal cell (LC) remains constant within a predetermined tolerance upon a change in the times of the state of high transmission (Ton);

wherein the at least one sensor (IL, IR) measures the brightness of the visible light incident thereon exclusively in the times of the low transmission state (Toff).

According to an embodiment of an invention, a system for the color coding of objects in the field of view of a plurality of spectacle wearers is provided herein. The system having:

a pair of spectacles per spectacle wearer, with respectively at least one spectacle lens;

wherein the respective at least one spectacle lens comprises a liquid crystal cell (LC), the transmission of which may be varied by a suitable control;

wherein the liquid crystal cells (LC) are so designed that the transmission (TR) of the liquid crystal cells (LC) may be switched between high and low transmission states; and with means for regulating or controlling the times of the high transmission (Ton) states of the liquid crystal cells (LC) such that the respective liquid crystal cells (LC) are set to high transmission (Ton) states at different times; and with one RGB light source (S1, S2, S3) per spectacle wearer;

means for controlling or regulating the luminance times, the color and the intensity of the RGB light source (S1, S2, S3) such that the RGB light source (S1) for a first spectacle wearer illuminates with a first color at a time of the state of high transmission (Ton) of the liquid crystal cell (LC) of their spectacles; and that the RGB light source (S2) for a second spectacle wearer illuminates at a time of high transmission (Ton) of the liquid crystal cell (LC) of the spectacles of the second spectacle wearer with a second color different from the first.

According to an embodiment, the system is characterized in that in the times of the state of low transmission (Toff) of the respective spectacles, the associated RGB light sources (S1, S2, S3) emit those colors that are necessary in order to produce, in a temporal mean, a white color impression in persons not wearing any of the spectacles.

According to an embodiment, the system is characterized in that the liquid crystal cell (LC) of a first spectacle wearer has an attenuated but non-zero transmission in a time of the state of high transmission (Ton) of a second spectacle wearer.

According to an embodiment, the system is characterized in that the color in which the RGB light source for the first spectacle wearer illuminates at a time of the state of high transmission (Ton) of the liquid crystal cell (LC) of their spectacles may be freely defined through an arbitrary intensity value between 0% and 100% of a color component of each primary color of its RGB light source (S1);

while the missing fraction to 100% is emitted for each of the three primary colors of their RGB light source (S1) at the associated time of the low transmission state (Toff) of the liquid crystal cell (LC).

According to an embodiment, the system is characterized in that the spectacles each comprise at least one sensor (IL, IR) for measuring the brightness of the visible light incident on them;

wherein the respective at least one sensor (IL, IR) is arranged on the eye-side of the respective spectacle lens;

wherein the respective at least one sensor (IL, IR) measures the brightness through the at least one spectacle lens;

and with a closed-loop control circuit (MC) each for controlling the transmission of the respective liquid crystal cell (LC);

wherein a setpoint value is preset for the brightness at the eye of the respective spectacle wearer;

wherein the control circuit (MC) takes the brightness measured by the at least one sensor (IL, IR) as the actual value.

According to an embodiment, the system is characterized in that an additional LED that can address the sensor in order to check the proper functioning of the liquid crystal cell of the respective spectacles for safety reasons.

According to an embodiment, a method for the color coding of objects in the field of view of a plurality of spectacle wearers is provided herein. The method, comprises the following:

each spectacle wearer wears spectacles, with in each case at least one spectacle lens;

wherein the respective at least one spectacle lens comprises a liquid crystal cell (LC), the transmission of which may be varied by a suitable control;

wherein the liquid crystal cells (LC) are so designed that the transmission (TR) of the liquid crystal cells (LC) may be switched between high and low transmission states; and wherein the times of the high transmission states (Ton) of the respective liquid crystal cells (LC) are set to high transmission states (Ton) at different times;

an RGB light source (S1, S2, S3) is provided for each spectacle wearer;

the luminance times, the color and the intensity of the RGB light sources (S1, S2, S3) are controlled such that the RGB light source (S1) for a first spectacle wearer illuminates with a first color at a time of the state of high transmission (Ton) of the liquid crystal cell (LC) of their spectacles; and that the RGB light source (S2) for a second spectacle wearer illuminates at a time of high transmission (Ton) of the liquid crystal cell (LC) of the spectacles of the second spectacle wearer with a second color that is different from the first.

According to an embodiment, a system is provided herein; wherein spectacles for a wearer with at least two eyes, a right (E(R)) and a left (E(L)) eye, with one spectacle lens in front of each of the two eyes;

wherein each spectacle lens comprises a liquid crystal cell (LC(L), LC(R)), the transmission of which may be varied by a suitable control;

wherein the liquid crystal cells (LC(L), LC(R)) are so designed that the transmission (TR) of the liquid crystal cells may be switched between high and low transmission states, respectively; and with means for controlling or regulating the times of the high transmission states (Ton) of the liquid crystal cells (LC(L), LC(R)); and with two light sources (S1(L), S1 R)) each associated with one eye;

wherein the two light sources emit different colors, and wherein the stereoscopic base (DS1) of the light sources is greater than the eye distance (PD); and with means for controlling or regulating the lighting times of the light sources (S1(L), S1(R)) in such a way that the light source (S1(R)) associated with the right eye (E(R)) illuminates during a high transmission state (Ton) of the liquid crystal cell (LC(R)) of the right eye, while the light source (S1(L)) associated with the left eye (E(L)) does not illuminate, and the liquid crystal (LC(L)) of the left eye is set to low transmission;

and vice versa.

According to an embodiment, the system is characterized in that the color emitted by the respective light sources at the times of the high transmission states (Ton) is supplemented during the associated times of the low transmission (Toff) states to give a white color impression, According to an embodiment, the system is characterized in that the two light sources are amplitude-modulated with a predetermined frequency which may be perceived by the human eye.

According to an embodiment, the system is characterized in that the spectacles comprise at least one sensor (IL, IR) for measuring the brightness of the visible light incident thereon;

wherein the at least one sensor (IL, IR) is arranged on the eye-side of the at least one spectacle lens;

wherein the at least one sensor (IL, IR) measures the brightness through the at least one spectacle lens; and with at least one closed-loop control circuit (MC) for regulating the transmission of the respective liquid crystal cell (LC);

wherein at least one setpoint value is preset for the brightness at the eye of the spectacle wearer;

wherein the control circuit (MC) takes the brightness measured by the at least one sensor as the actual value.

According to an embodiment of an invention, a method for enhancing the spatial impression of an object, comprising the following is provided herein:

spectacles are provided for a wearer with at least two eyes, a right (E(R)) and a left (E(L)) eye, wherein the spectacles have a respective spectacle lens in front of each of the two eyes;

wherein each spectacle lens comprises a liquid crystal cell (LC(L), LC(R)), the transmission of which may be varied by a suitable control;

wherein the liquid crystal cells (LC(L), LC(R)) are so designed that the transmission (TR) of the liquid crystal cells may be respectively switched between high and low transmission states;

the times of the high transmission states (Ton) of the liquid crystal cells (LC(L), LC(R)) are controlled;

two light sources (S1 (L), S1 (R)) are further provided, each being associated with one eye;

wherein the two light sources emit different colors, and wherein the stereoscopic base (DS1) of the light sources is greater than the eye distance (PD);

the lighting times of the light sources (S1(L), S1(R)) are controlled such that the light source (S1(R)) associated with the right eye (E(R)) illuminates during a high transmission state (Ton) of the liquid crystal cell (LC(R)) of the right eye, while the light source (S1(L)) associated with the left eye (E(L)) does not illuminate, and the liquid crystal (LC(L)) of the left eye is set to low transmission;

and vice versa.

According to an embodiment of an invention, a system for improving the view of an area to be monitored spatially by means of glare suppression is provided herein. The system having spectacles, with at least one spectacle lens;

wherein the at least one spectacle lens comprises a liquid crystal cell (LC) whose transmission (TR) may be varied by a suitable control;

wherein the liquid crystal cell (LC) is so designed that the transmission (TR) of the liquid crystal cell (LC) may be switched between high and low transmission states; and with means for regulating or controlling the times of the state of high transmission (Ton) of the liquid crystal cell (LC);

a pulsed light source (S) which emits light pulses;

wherein the light source (S) is so designed that it can generate light pulses whose temporal duration is shorter than the time that the light of the light source needs to traverse the area to be monitored spatially in the viewing direction of the wearer; and with means for controlling or regulating the times of the state of high transmission (Ton) of the liquid crystal cell (LC) that are able to temporally arrange the times of the state of high transmission (Ton) of the liquid crystal cell so that only the backscattering signal of the light pulse from the area to be monitored spatially is transmitted by the liquid crystal cell (LC).

According to an embodiment, the system is characterized in that the spectacles comprise at least one sensor (IL, IR) for measuring the brightness of the visible light incident thereon;

wherein the at least one sensor (IL, IR) is arranged on the eye-side of the respective spectacle lens;

the at least one sensor (IL, IR) measures the brightness through the at least one spectacle lens; and with at least one closed-loop control circuit (MC) for controlling the transmission of the respective liquid crystal cell (LC);

wherein a setpoint value is preset for the brightness at the eye of the spectacle wearer;

wherein the control circuit (MC) takes the brightness measured by the at least one sensor (IL, IR) as the actual value.

According to an embodiment of an invention, a method for improving the view of an area to be monitored spatially by means of glare suppression is provided herein; the method comprising the following:

spectacles are provided, wherein the spectacles comprise at least one spectacle lens;

wherein the at least one spectacle lens comprises a liquid crystal cell (LC), the transmission (TR) of which may be varied by a suitable control;

wherein the liquid crystal cell (LC) is so formed that the transmission (TR) of the liquid crystal cell (LC) may be switched between high and low transmission states;

the times of the state of high transmission (Ton) of the liquid crystal cell (LC) are controlled; a pulsed light source (S) which emits light pulses is provided;

wherein the light source (S) is so designed that it can generate light pulses whose temporal duration is shorter than the time that the light of the light source needs to traverse the area to be monitored spatially in the viewing direction of the wearer;

further, the times of the state of high transmission (Ton) of the liquid crystal cell are so arranged temporally that only the backscattering signal of the light pulse from the area to be monitored spatially is transmitted by the liquid crystal cell (LC).

Thus, spectacles are proposed. The spectacles have a spectacle lens with a liquid crystal cell LC, the transmission TR of which may be switched between transmitting and blocking. Furthermore, the spectacles have an eye tracker ET, which can determine the viewing direction of the eye. Furthermore, at least one sensor IL, IR is provided to measure the brightness of the visible light incident thereon, wherein the sensor is arranged on the eye-side of the spectacle lens 30 and measures the brightness by the at least one spectacle lens in a spatially resolved manner. The sensor can determine the brightness of the visible light from the viewing direction of the eye determined with the eye tracker. The spectacle also has a closed-loop control circuit for the control of the transmission of the liquid crystal cell, wherein a setpoint value for the brightness is preset at the eye, and wherein the control circuit takes the brightness measured by the sensor in the viewing direction of the eye as the actual value.

The invention claimed is:

1. Spectacles for a wearer with at least one eye, comprising:
   1.1 at least one spectacle lens;
   1.1.1 wherein the at least one spectacle lens comprises a liquid crystal cell (LC), the transmission (TR) of which may be varied by a suitable control;
   1.2 an eye tracker (ET) capable of determining the viewing direction of the eye;
   1.3 at least one sensor (IL, IR) for measuring the brightness of the visible light incident thereon;
   1.3.1 wherein the at least one sensor (IL, IR) is arranged on the eye-side of the spectacle lens;
   1.3.2 wherein the at least one sensor (IL, IR) can measure the brightness through the at least one spectacle lens;
   1.3.3 wherein the at least one sensor (IL, IR) comprises
   1.3.3.1 an imaging system with a camera or
   1.3.3.2 at least three sensors that span a coordinate system or
   1.3.3.3 a compound eye;
   1.3.4 wherein the at least one sensor (IL, IR) is able to determine the brightness of the visible light which is incident upon it from the viewing direction of the eye determined by the eye tracker (ET); and
   1.4 a closed-loop control circuit (MC) to control the transmission of the liquid crystal cell (LC);

1.4.1 wherein a setpoint value for the brightness at the eye is preset;
1.4.2 wherein the control circuit takes the brightness measured by the at least one sensor (IL, IR) in the viewing direction of the eye as the actual value.

2. Spectacles according to claim 1,
wherein
the liquid crystal cell (LC) is so designed that it can change its transmission from 90% to 10% and from 10% to 90% in a maximum of 10 ms.

3. Spectacles according to claim 2,
wherein
3.1 the liquid crystal cell (LC) is so designed that the transmission (TR) of the liquid crystal cell (LC) may be switched between states of high and low transmission;
3.2 means are provided for controlling or regulating the times of the state of high ($T_{on}$) and low ($T_{off}$) transmission of the liquid crystal cell (LC) as well as the change between these two states;
3.2.1 wherein the control or regulation and the closed-loop control circuit (MC) are so designed that the times of the state of high transmission ($T_{on}$) become shorter with increasing brightness of the visible light incident on the at least one sensor (IL, IR);
3.2.2 wherein the change between the states of high ($T_{on}$) and low ($T_{off}$) transmission takes place with a temporal frequency which the human eye cannot resolve.

4. Spectacles according to claim 1,
wherein
the control circuit is so designed that, when determining the brightness from the viewing direction of the eye, it can take into account a user-specific eye/retina sensitivity curve for weighting the brightness.

5. Spectacles according to claim 1,
further comprising:
a spectacle frame (F), wherein
the spectacle frame seals the eye assigned to the at least one spectacle lens against the ambient light in a light-tight manner.

6. Spectacles according to claim 1,
wherein
the setpoint value of the control circuit prescribes a brightness at the eye of 20 to 400 lx.

7. Spectacles according to claim 1,
wherein
the brightness of the ambient light is derived from the setpoint value and a control signal of the control circuit.

8. Spectacles according to claim 1,
wherein
at least one further brightness sensor (OL, OR) is arranged on the side of the spectacles facing away from the eye (external sensor) and determines the brightness of the ambient light.

9. Spectacles according to claim 7,
wherein
9.1 the setpoint value of the control circuit may be changed as a function of the brightness of the ambient light; and
9.2 the change in the setpoint value is slower than the control of the transmission of the liquid crystal cell by a factor of at least 10.

10. Spectacles according to claim 9,
wherein
10.1 the setpoint value is changed in preset steps;
10.2 wherein the stepwise change of the setpoint value is slower than the control of the transmission of the liquid crystal cell by at least a factor of 100.

11. Spectacles according to claim 10,
wherein
the control is so designed that it reacts to extreme brightness values within 10 µs to one second such that the liquid crystal cell (LC) is set to the state of low transmission.

12. Spectacles according to claim 1,
further comprising:
12.1 two spectacle lenses for two eyes of a spectacle wearer;
12.2 an eye-side sensor for each spectacle lens for measuring the brightness of the visible light incident on the respective eye; and
12.3 a control circuit for each spectacle lens.

13. Spectacles according to claim 12,
wherein
the setpoint values for the two eyes differ from one another by 1% to 60%.

14. Spectacles according to claim 12,
wherein
when regulating the brightness of the visible light incident on an eye the regulation of the brightness for the other eye is taken into account.

15. Spectacles according to claim 1,
further comprising:
15.1 at least one light source (S) arranged on the side of the spectacles facing away from the eye;
15.2 wherein the light source may be controlled as a function of the viewing direction of the spectacle wearer.

16. Spectacles according to claim 15,
further comprising:
16.1 means for controlling the lighting times and the luminous intensity of the light source (S) such that it illuminates during the times of the state of high transmission ($T_{on}$) of the liquid crystal cell (LC);
16.2 wherein the temporal integral of the product of
16.2.1 the luminous intensity of the light source (S) and
16.2.2 the transmission (TR) of the liquid crystal cell (LC) remains constant within a predetermined tolerance upon a change in the times of the state of high transmission ($T_{on}$).

17. Spectacles according to claim 1,
further comprising:
a light source for the dazzling of a living being, an optical sensor or a camera, and/or
a display on the side of the spectacle lens facing away from the eye, and/or
a display on the eye-side of the spectacle lens, and/or
a head-up display (HUD).

18. Spectacles according to claim 1,
wherein
19.1 the at least one spectacle lens has a further liquid crystal cell, the transmission of which may be varied by a suitable control,
19.2 wherein the further liquid crystal cell is arranged behind or in front of the liquid crystal cell (LC) in the viewing direction.

19. Method for regulating the brightness of the visible light incident on at least one eye comprising the following steps:
21.1 a pair of spectacles is provided, wherein the spectacles comprise:
21.1.1 at least one spectacle lens;
21.1.2 wherein the at least one spectacle lens has a liquid crystal cell (LC), the transmission (TR) of which may be varied by a suitable control;

21.2 an eye tracker (ET) which determines the viewing direction of the eye;
21.3 at least one sensor (IL, IR) for measuring the brightness of the visible light incident on the sensor is provided;
21.3.1 wherein the at least one sensor (IL, IR) is arranged on the eye-side of the spectacle lens;
21.3.2 wherein the at least one sensor (IL, IR) measures the brightness through the at least one spectacle lens;
21.3.3 wherein the at least one sensor (IL, IR) comprises
21.3.3.1 an imaging system with a camera or
21.3.3.2 at least three sensors which span a coordinate system or
21.3.3.3 a compound eye;
21.3.4 wherein the at least one sensor (IL, IR) determines the brightness of the visible light from the viewing direction of the eye determined by the eye tracker (ET);
21.4 a closed-loop control circuit (MC) for controlling the transmission of the liquid crystal cell (LC) is provided;
21.4.1 wherein a setpoint value for the brightness at the eye is preset;
21.4.2 wherein the control loop takes the brightness measured by the sensor in the viewing direction of the eye as the actual value.

20. Spectacles according claim 8, wherein 101.1 the setpoint value of the control circuit may be changed as a function of the brightness of the ambient light; and 101.2 the change in the setpoint value is slower than the control of the transmission of the liquid crystal cell by a factor of at least 10.

21. Spectacles according to claim 20, wherein 102.1 the setpoint value is changed in preset steps;

102.2 wherein the stepwise change of the setpoint value is slower than the control of the transmission of the liquid crystal cell by at least a factor of 100.

22. Spectacles according to claim 21, wherein the control is so designed that it reacts to extreme brightness values within 10 µs to one second such that the liquid crystal cell (LC) is set to the state of low transmission.

* * * * *